(12) United States Patent
Ahn et al.

(10) Patent No.: US 8,722,110 B2
(45) Date of Patent: May 13, 2014

(54) **PHARMACEUTICAL COMPOSITION FOR PREVENTING OR TREATING INFLAMMATORY DISEASES, ALLERGIC DISEASES OR ASTHMA, CONTAINING *DIOSPYROS BLANCOI* A. DC. EXTRACT AS ACTIVE INGREDIENT**

(75) Inventors: Kyung Seop Ahn, Daejeon (KR); Ok-Kyoung Kwon, Daejeon (KR); Sei Ryang Oh, Daejeon (KR); Jung Hee Kim, Daejeon (KR); Hyeong Kyu Lee, Daejeon (KR); Mee-Young Lee, Daejeon (KR); Hwa-Young Son, Daejeon (KR); Kyoung-Youl Lee, Daejeon (KR); Soo Yong Kim, Daejeon (KR); Giselle Tomayo-Castillo, Heredia (CR); Katia Rosales-Ovares, Heredia (CR); Rodrigo Gamez-Lobo, Heredia (CR)

(73) Assignee: Korea Research Institute of Bioscience and Biotechnology, Daejon (KR)

( * ) Notice: Subject to any disclaimer, the term of this patent is extended or adjusted under 35 U.S.C. 154(b) by 0 days.

(21) Appl. No.: 13/820,474

(22) PCT Filed: Aug. 30, 2011

(86) PCT No.: PCT/KR2011/006403
§ 371 (c)(1),
(2), (4) Date: Mar. 1, 2013

(87) PCT Pub. No.: WO2012/030137
PCT Pub. Date: Mar. 8, 2012

(65) Prior Publication Data
US 2013/0164395 A1  Jun. 27, 2013

(30) Foreign Application Priority Data

Sep. 3, 2010 (KR) .................. 10-2010-0086356
Mar. 3, 2011 (KR) .................. 10-2011-0018950

(51) Int. Cl.
*A01N 65/00* (2009.01)

(52) U.S. Cl.
USPC .......................................... 424/725

(58) Field of Classification Search
None
See application file for complete search history.

(56) References Cited

U.S. PATENT DOCUMENTS 5,854,010 A  12/1998 Denison et al.

FOREIGN PATENT DOCUMENTS

KR  1019990050893  11/1999

OTHER PUBLICATIONS

Ragasa et al., "Bioactive triterpenes from *Diospyros blancoi*", Natural Product Research, 23:1252-1258. 2009 .

*Primary Examiner* — Michael Meller
(74) *Attorney, Agent, or Firm* — Cheryl H. Agris; Agris & von Natzmer LLP

(57) ABSTRACT

Disclosed is a pharmaceutical composition for the prophylaxis and therapy of inflammatory diseases, allergic diseases, or asthma, comprising a velvet apple (*Diospyros blancoi* A. DC.) extract as an active ingredient. Having the inhibitory activity against the nuclear translocation of NF-κB, whose level is rapidly elevated in response to inflammatory stimuli, the velvet apple extract can suppress the production of NO and $PGE_2$, the expression of iNOS and COX-2, and the release of IL-1β and TNF-α, and can significantly down regulate Th2-mediated IL-4 and IL-13 production. In addition, the extract was found to inhibit the activation of eosinophils in bronchoalveolar lavage fluid, and to suppress the secretion of immunoglobulins and chemokines in bronchoalveolar lavage fluid and blood, as measured by in vivo tests on an ovalbumin-induced asthma mouse model. Therefore, the extract can be used in the method for preventing or treating various inflammatory disorders, allergic diseases, or asthma.

1 Claim, 10 Drawing Sheets

PHARMACEUTICAL COMPOSITION FOR PREVENTING OR TREATING INFLAMMATORY DISEASES, ALLERGIC DISEASES OR ASTHMA, CONTAINING *DIOSPYROS BLANCOI* A. DC. EXTRACT AS ACTIVE INGREDIENT

TECHNICAL FIELD

The present invention relates to a pharmaceutical composition for the prophylaxis and therapy of inflammatory diseases, allergic diseases, or asthma, comprising a velvet apple (*Diospyros blancoi* A. DC.) extract as an active ingredient.

BACKGROUND ART

Inflammation is a pathological condition of an abscess caused by foreign infectious agents (bacteria, fungi, virus, various kinds of allergens, etc.). For example, when foreign bacteria invade into and proliferate in a tissue, the leukocytes of the body recognize and actively attack the proliferating foreign bacteria, during which leukocytes die and bacteria are killed by the leukocytes. The dead leukocytes and bacterial lysates accumulate in the tissue, forming an abscess. The abscess formed by inflammation can be treated through anti-inflammation activity. Anti-inflammation activity refers to a process that reduces inflammation in which the proliferation of the foreign agent, such as bacteria, is inhibited with the aid of an anti-inflammatory agent, for example, an antibacterial agent, or in which macrophages are activated to digest and excrete the foreign materials accumulated in the abscess.

Inflammation refers to a biological protective response of tissues to harmful stimuli. Inflammation is a protective attempt by the organism to remove the injurious stimuli and to initiate the healing process for rehabilitating the cells or tissues on which organic lesion has been imposed by the invasion of the stimuli. Factors involved in these serial processes are local vascular tissues, various tissue cells of the body fluid, immune cells, etc. With advances of molecular biology, attempts have recently been made to understand inflammatory diseases at molecular levels. As a result, factors responsible for inflammatory diseases have been gradually revealed.

Cytokines and mediators which induce inflammation are regulated by nuclear factors. To quote an example, NF-κB (nuclear factor-kappa B) is a nuclear protein of the Rel gene family, and to date, seven members of the NF-κB subfamily have been identified. While in an inactivated state, NF-κB is located in the cytosol, complexed with the inhibitory protein IκB (inhibitory kappa B). A variety of extracellular signals including reactive oxygen, chemokines such as TNF-α (tumor necrosis factor-α), and LPS (lipopolysaccharide) activate the enzyme IκB kinase. In turn, the IκB kinase phosphorylates IκB, which results in dissociation of IκB from NF-κB. The NF-κB thus activated, a heterodimer composed of p50 and p65, is then translocated into the nucleus where it binds to specific sequences of DNA to promote the expression of the target genes, for example, genes responsible for inflammation, such as tumor necrosis factor, cyclooxygenase, etc. (Oh G T et al., *Artherosclerosis,* 159(1): 17-26, 2001; Epstein F H et al., *The New England Journal of Medicine*, 336(15): 1066-1071, 1997; Zhang W J et al., *FASEB J*, 15(130): 2423-2431, 2001; Denk A et al., *J. Biol. Chem.*, 276(30): 28451-28458, 2001; Sahnoun Z et al., *Physiology*, 53(4): 315-339, 1998; Lindner V *Pathobiology*, 66(6): 311-320, 1998; Landry D B et al., *Am. J. Pathol.*, 151(4): 1085-1095, 1997; Gerritsen M E et al., *Am. J. Pathol.*, 147(2): p278-292, 1995).

Nitric oxide is biosynthesized endogenously by the oxidation of L-arginine in the presence of nitric oxide synthase (NOS), and is an inflammatory mediator acting as a host defense by damaging pathogenic DNA and as a regulatory molecule with homeostatic activities (Kou and Schroder, Annals of Surgery 221, 220-235, 1995). In the NOS family, iNOS (inducible nitric oxide synthase) is known to be closely correlated with the intracellular overproduction of NO. $PGE_2$ (prostaglandin $E_2$) and leukotriene are inflammatory mediators that are biosynthesized from arachidonic acid. $PGE_2$ is produced by the cyclooxygenase-2 enzyme (COX-2) and is abundantly found in macrophages and monocytes. Macrophages are induced by inflammatory agents, such as LPS, to be activated.

Asthma is a disease characterized by hypersensitivity of the airways to a variety of stimuli and results in variable and recurring symptoms including wheezing, shortness of breath, coughing, etc. which are often reversible either spontaneously or with specific therapy. Most asthma is allergic with symptoms of chronic airway inflammation and bronchial hyperresponsiveness (Minoguchi K and Adachi M. Pathophysiology of asthma. In: Chemiack N S, Altose M D, Homma I, editors. Rehabilitation of the patient with respiratory disease. New York: McGraw-Hill, 1999, pp 97-104).

Asthma may be classified as extrinsic or intrinsic based on whether symptoms are precipitated by allergens (extrinsic) or not (intrinsic). Patients with extrinsic asthma test positive in a skin test for allergies and in a bronchial provocation test, and extrinsic asthma is usually developed from childhood. Dust and dust mites are prevalent among allergens. In addition, pollen, epithelia from animals, and fungi are causative of asthma. For intrinsic asthma, symptoms occur or worsen in the presence of upper respiratory tract infections, exercise, emotional instability, cold weather, and moisture changes, and is observed in adult patients. Further, there are chemical-induced asthma, exercise-induced asthma, and occupational asthma.

Generally, asthma is known as a chronic inflammatory disease which is developed as inflammatory cells, after proliferation, differentiation, and activation by interleukin-4, -5, and -13 produced by Th2 (T helper 2) lymphocytes, migrate and invade the airways and tissues around the airways (Elias J A, et al., *J. Clin. Invest.*, 111, pp 291-297, 2003). In this case, activated inflammatory cells such as eosinophils, mast cells, alveolar macrophages, etc. release various inflammatory mediators (cysteinyl leukotrienes, prostaglandins, etc.), playing an important role in bronchial constriction (Maggi E, *Immunotechnology*, 3, pp 233-244, 1998; Pawankar R., *Curr. Opin. Allergy Clin. Immunol.*, 1, pp 3-6, 2001; Barnes P J, et al., *Pharmacol Rev.*, 50, pp 515-596, 1998).

Accordingly, because cytokines IL-4, IL-5, and IL-13 and immunoglobulin, which are involved in the activation of inflammatory cells, and cysteinyl leukotrienes secreted from the inflammatory cells such as eosinophils, are main factors causing asthma, extensive research has been done to develop drugs inhibitory of the production or biosynthesis of the factors.

Steroid agents are the most potent anti-inflammatory drugs developed thus far. However, the long-term use of steroids is accompanied by side effects. In the treatment of asthma, steroid agents exert surprising therapeutic effects to the extent of completely removing the symptoms the first time, but this is transient. Symptoms revive with the cessation of use of steroids and are exacerbated with the repetition of their use. Sides effects of steroids include the development of a round, puffy face, fluid collection, adrenal insufficiency, an increase in susceptibility to infections, the occurrence of neurological problems, exacerbation of cataracts, glaucoma, and gastric ulcers, a delay in wound healing, and reactivation of latent infections.

Studies have been focused on materials which have anti-inflammatory effects without side effects. Particularly, extracts from plants which are inhibitory of inflammation and are safely applicable to foods without causing side effects have attracted intensive scientific interest. For example, with the fact in mind that NF-κB, a regulator of a gene population responsible for atopic dermatitis, binds to specific genes of immune cells to promote the expression of inflammatory mediators, a research team from Hirosaki University, Japan, in collaboration with a team from Osaka University, Japan, developed an atopy therapeutic comprising an artificial DNA mimicking the gene to which NF-κB binds, which blocks the activity of NF-κB by tricking NF-κB into the artificial DNA mimic, and demonstrated the clinical effectiveness of the therapeutic. Novartis Pharma A. G. in Basel, Switzerland, developed and markets "Elidel" derived from pimecrolimus, as a therapeutic for atopic dermatitis, which is an ascomycin macrolactam derivative functioning to selectively inhibit the synthesis and release of cytokines responsible for inflammation. In addition, a research team led by Prof. H. W. Chang in the College of Pharmacy, Yeungnam University, found that an extract from Saururus chinensis (Lour.) Baill and Ailanthus altissima SWINGLE is therapeutically effective for asthma and allergies, and was reported to have agreed on a contract with Korea Pharma Co. Ltd on Jan. 19, 2006 for technical transfer at a royalty of 4% of sales with a prepayment of 150 million won (from a report on Jan. 22, 2006, of the Korean Pharmaceutical Association News).

Many therapeutics for allergic and inflammatory diseases have been developed to target cytokines and chemokines involved in the onset of the diseases. Among them are compositions comprising kiwi fruit extracts, fermented cactus extracts, and lactic acid bacteria. Nowhere is the use of a velvet apple extract in the therapy of inflammation and asthma found in the prior art.

Velvet apple, also called Mabolo or Kamagong, is a plant of the genus of ebony trees belonging to the Ebenaceae family. It is native to the Philippines. Velvet apple timber is extremely dense and hard and is famous for its dark color. Like many other very hard woods, it is sometimes called "iron wood." Its edible fruit has a skin covered in a fine, velvety fur which is usually reddish-brown, and soft, creamy, pink flesh, with a taste and aroma comparable to fruit cream cheese (Benedikt Mandl, Jimmy Wales, Wikimedia Foundation, 2004). U.S. Patent Publication No. 20080199533 discloses the use of velvet apple fruits as a cosmetic material. In addition, velvet apple fruits are used as food materials. A recent report has described that a mixture of several chemicals separated from an ethylacetate extract of spontaneously dried velvet apple leaves have analgesic and anti-inflammatory effects as demonstrated in a mouse test (Ragasa C Y et al., Nat. Prod. Res. 23(13): 1252-1258, 2009), but did not elucidate the mechanism of anti-inflammation or anti-asthmatic effects.

We, the present inventors, made an experiment to discover the anti-inflammation mechanism of a velvet apple extract. Artificial inflammation-induced macrophages, when treated with a velvet apple extract, were found to inhibit the nuclear translocation of NF-κB whose expression is promoted in response to inflammatory stimuli, which in turn suppresses the production of NO and $PGE_2$, the expression of iNOS and COX-2, and the release of IL-1β and TNF-α, and significantly down-regulates Th2-mediated IL-4 and IL-13 production. In addition, an ovalbumin-induced asthma mouse model test showed that a velvet apple extract inhibits the increase of eosinophils in bronchoalveolar lavage fluid and suppresses the secretion of immunoglobulins and chemokines in bronchoalveolar lavage fluid and blood. Also, the velvet apple extract is found to be almost free of cytotoxicity and therefore is useful as an active ingredient of a pharmaceutical composition for preventing or treating various inflammatory disorders, allergic diseases, or asthma, which leads to the present invention.

DISCLOSURE

Technical Problem

It is therefore an object of the present invention to provide a pharmaceutical composition, a topical dermatologic agent, a cosmetic composition, and a health food for the prophylaxis and therapy or amelioration of inflammatory diseases, allergic diseases, or asthma, comprising a velvet apple (*Diospyros blancoi* A. DC.) extract as an active ingredient.

It is another object of the present invention to provide a method for preventing or treating inflammatory diseases, allergic diseases, or asthma, using a velvet apple (*Diospyros blancoi* A. DC.) extract.

Technical Solution

In accordance with an aspect thereof, the present invention provides a pharmaceutical composition for the prophylaxis and therapy of an inflammatory disease, an allergic disease or asthma, comprising a velvet apple (*Diospyros blancoi* A. DC.) extract as an active ingredient.

In accordance with another aspect thereof, the present invention provides a topical dermatologic agent for the prophylaxis and therapy of an inflammatory disease, an allergic disease or asthma, comprising a velvet apple extract as an active ingredient.

In accordance with a further aspect thereof, the present invention provides a cosmetic composition for the prophylaxis and amelioration of an inflammatory disease, an allergic disease or asthma, comprising a velvet apple extract as an active ingredient.

In accordance with still a further aspect thereof, the present invention provides a health food for the prophylaxis and amelioration of an inflammatory disease, an allergic disease or asthma, comprising a velvet apple extract as an active ingredient.

In accordance with still another aspect thereof, the present invention provides a method for treating an inflammatory disease, an allergic disease or asthma, comprising administering a pharmaceutically effective amount of a velvet apple extract to a subject in need thereof.

In accordance with yet another aspect thereof, the present invention provides a method for preventing an inflammatory disease, an allergic disease or asthma, comprising administering a pharmaceutically effective amount of a velvet apple extract to a subject in need thereof.

In accordance with yet still another aspect thereof, the present invention provides a velvet apple extract for use in a pharmaceutical composition for the prophylaxis and therapy of an inflammatory disease, an allergic disease or asthma.

In accordance with yet a further aspect thereof, the present invention provides a velvet apple extract for use in a topical dermatologic agent for the prophylaxis and therapy of an inflammatory disease, an allergic disease or asthma.

In accordance with an additional aspect thereof, the present invention provides a velvet apple extract for use in a cosmetic composition for the prophylaxis and therapy of an inflammatory disease, an allergic disease or asthma.

In accordance with still an additional aspect thereof, the present invention provides a velvet apple extract for use in a health food for the prophylaxis and therapy of an inflammatory disease, an allergic disease or asthma.

Unless stated otherwise, or implicit from context, the following terms and phrases include the meanings provided below.

As used herein, the term "inflammation" is intended to encompass a pathological condition of abscess formed by the invasion of a foreign infectious agent (bacteria, fungi, virus, various allergens).

The term "allergy," as used herein, is intended to encompass an abnormal response to a foreign agent of the organism in contact with the foreign agent.

The term "prophylaxis," "prevention," or "preventing," as used herein, is intended to refer to any action resulting in the suppression or delay of the onset or progression of inflammatory diseases thanks to the administration of the pharmaceutical composition according to the present invention.

The term "treatment," "therapy," "treating," "amelioration," or "ameliorating," as used herein, is intended to refer to any action resulting in improvement in symptoms of inflammatory diseases or the beneficial alteration of the inflammatory state thanks to the administration of the composition according to the present invention.

As used herein, the term "administration" is intended to encompass providing a subject with the composition of the present invention using any suitable method.

As used herein, the term "subject" is intended to encompass a patient, such as a human, a monkey, a dog, a goat, a pig, or a rat, with an inflammatory disease whose symptoms can be improved or beneficially altered by administering the composition of the present invention.

The term "therapeutically effective amount," as used herein, is intended to refer to a sufficient amount of the composition to treat a disorder, at a reasonable benefit/risk ratio applicable to any medical treatment. The effective amount may vary depending on various factors including the kind of disorder being treated, the severity of the disorder being treated, the activity of the drug, sensitivity to the drug, the time of administration, the route of administration, the rate of excretion, the period of time of treatment, co-administration of drugs, etc.

A detailed description will be given of the present invention below.

The present invention addresses a pharmaceutical composition for the prophylaxis and therapy of an inflammatory disease, an allergic disease, or asthma, comprising a velvet apple (*Diospyros blancoi* A. DC.) extract as an active ingredient.

Examples of the inflammatory disease treatable in the present invention include dermatitis, atopy, conjunctivitis, perodontitis, rhinitis, otitis media, laryngopharyngitis, tonsillitis, pneumonia, gastric ulcer, gastritis, Crohn's disease, colitis, hemorrhoid, gout, ankylosing spondylitis, rheumatic fever, lupus, fibromyalgia, psoriatic arthritis, osteoarthritis, rheumatoid arthritis, periarthritis shoulder, tendonitis, tenosynovitis, peritendinitis, myositis, hepatitis, cystitis, naphritis, Sjogren's syndrome, multiple sclerosis, and acute and chronic inflammatory diseases, but are not limited thereto.

The velvet apple (*Diospyros blancoi* A. DC.) extract useful in the present invention may be prepared by a method comprising, but not limited to, the following steps:

1) adding an extraction solvent to velvet apple (*Diospyros blancoi* A. DC.) to afford an exudate;
2) filtering the exudate of step 1); and
3) concentrating the filtrate of step 2) in vacuo to dryness.

In step 1), any velvet apple (*Diospyros blancoi* A. DC.), whether cultivated or purchased, may be used. The parts of velvet apple (*Diospyros blancoi* A. DC.) that are useful in the present invention are preferably leaves, stems, and roots.

As the extraction solvent, water, alcohol, or a mixture thereof may be preferably used. The alcohol may be a $C_1$ or $C_2$ lower alcohol, that is, methanol or ethanol. The extraction may be conducted using, but not limited to, a shaking extraction method, a Soxhlet extraction method, or a reflux extraction method. The extraction solvent is used in a volume of ten times as much as the dried velvet apple (*Diospyros blancoi* A. DC.). The extraction temperature may be preferably set within the range of from 30 to 100° C. Extraction is preferably continued for 10 to 48 hours, and more preferably for 15 to 30 hours. Also, the extraction may be preferably repeated three to five times, more preferably three times.

In step 3) of the method, the filtrate may be concentrated using, but not limited to, a centrifugal vacuum concentrator or a rotary vacuum evaporator. The concentrate may be dried using a vacuum drying method, a reduced-pressure drying method, a boiling drying method, a spray drying method, or a freeze drying method.

An examination was made to see whether a velvet apple (*Diospyros blancoi* A. DC.) extract inhibits the translocation of NF-κB into the nucleus. For this, macrophages were treated with lipopolysaccharide (LPS) to induce inflammation, and the translocation of NF-κB was observed using an immunofluorescence method. As a result, a lower population of NF-κB was detected in the nucleus of the cells treated with LPS in combination with a velvet apple (*Diospyros blancoi* A. DC.) extract than with LPS alone (FIG. 1).

To examine whether the velvet apple (*Diospyros blancoi* A. DC.) extract has a negative effect on the expression of iNOS protein and RNA, the expression of iNOS in the macrophages under LPS-induced inflammation was analyzed using Western blotting, PCR, and immunofluorescence. The level of iNOS in the cells treated with LPS in combination with a velvet apple (*Diospyros blancoi* A. DC.) extract was significantly lower than that in the cells treated with LPS alone (FIG. 2) Like iNOS, COX-2 was also analyzed for expression at protein and RNA levels. The cells co-treated with LPS and the velvet apple (*Diospyros blancoi* A. DC.) extract were observed to express COX-2 at significantly lower levels than did those treated with LPS only (FIG. 3).

An examination was made to see whether the production of NO and $PGE_2$ is affected upon the inhibition of the velvet apple (*Diospyros blancoi* A. DC.) extract against the expression of iNOS and COX-2. In this regard, levels of NO and $PGE_2$ in the macrophages under LPS-induced inflammation were measured on a microplate reader. Likewise, levels of both NO and $PGE_2$ were significantly decreased in the cells co-treated with LPS and the velvet apple extract, compared to the cells treated with LPS alone, in a manner dependent on the dose of the velvet apple extract (FIGS. 2 and 3).

Among the velvet apple (*Diospyros blancoi* A. DC.) extracts, the best extract in terms of cell viability and inhibitory activity against NO production was selected. Cells were treated with 5, 10, 20, 40, and 50 μg/ml of a methanol extract of velvet apple (*Diospyros blancoi* A. DC.), 5, 10, 20, and 40 μg/ml of a hexane extract of velvet apple (*Diospyros blancoi* A. DC.), 5, 10, 20, and 40 μg/ml of a chloroform extract of velvet apple (*Diospyros blancoi* A. DC.), 5, 10, 20, 40, and 50 μg/ml of an ethylacetate extract of velvet apple (*Diospyros* blancoi A. DC.), 5, 10, 20, and 40 µg/ml of a butanol extract of velvet apple (*Diospyros blancoi* A. DC.), and 5, 10, 20, and 40 µg/ml of a water extract of velvet apple (*Diospyros blancoi* A. DC.), and analyzed for cell viability and NO production. Almost no cytotoxicity was detected in the methanol extracts of velvet apple (*Diospyros blancoi* A. DC.), whereas the toxicity of the hexane extract, the chloroform extract, and the ethyl acetate extract increased with an increase in the dose thereof. Treatment with a methanol, a chloroform, or an ethylacetate extract reduced nitric oxide reduction. Accordingly, the methanol extract of velvet apple (*Diospyros blancoi* A. DC.) was determined to be the most effective ingredient in the pharmaceutical composition for the prophylaxis and therapy of inflammatory diseases, allergic diseases, or asthma as it is non-cytotoxic and significantly reduces NO production (Tables 1 and 2)

In addition, the inhibitory activity of the velvet apple (*Diospyros blancoi* A. DC.) extract against the release of tumor necrosis factor-α (TNF-α) and IL-1β was examined. Macrophages under LPS-induced inflammation were analyzed for TNF-α and IL-1β levels using respective enzyme immunometric kits (mouse TNF-α Enzyme Immunometric Assay Kit, and mouse IL-1β Enzyme Immunometric Assay Kit). The cells co-treated with LPS and the velvet apple (*Diospyros blancoi* A. DC.) extract were significantly low in the level of both TNF-α and IL-1β, compared to those treated with LPS alone, and the velvet apple (*Diospyros blancoi* A. DC.) extract reduced the levels of TNF-α and IL-1β in a dose-dependent manner (FIG. 4).

Also, the release of cytokines from splenocytes was examined in the presence of the velvet apple (*Diospyros blancoi* A. DC.) extract. Splenocytes were incubated with various doses of the velvet apple (*Diospyros blancoi* A. DC.) extract and then treated with concanavalin A. The velvet apple (*Diospyros blancoi* A. DC.) was found to reduce the levels of the ConA-induced cytokines IL-4 and IL-13 in a dose-dependent manner as measured by ELISA (FIG. 5).

Effects of the velvet apple (*Diospyros blancoi* A. DC.) were also examined in vivo using ovalbumin-induced asthma mice. In this regard, after the sensitization of the airways with ovalbumin, the mice were administered orally with the velvet apple (*Diospyros blancoi* A. DC.) extract. The extract was found to reduce the count of inflammatory cells and eosinophils in bronchoalveolar lavage fluid in a dose-dependent manner. (FIG. 6).

The velvet apple (*Diospyros blancoi* A. DC.) extract was also assayed for inhibitory activity against the production of immunoglobulins involved in allergy mechanism. In mice whose airways was sensitized with ovalbumin, levels of immunoglobulins were significantly low upon administration with the velvet apple (*Diospyros blancoi* A. DC.), compared to controls (FIG. 7).

In order to examine the inhibition of the velvet apple (*Diospyros blancoi* A. DC.) extract against eotaxin, which is implicated in allergic responses, chemokine levels were measured in the alveolar lavage fluid obtained after the sensitization of the airways with ovalbumin. The production of eotaxin was reduced by the administration of the velvet apple (*Diospyros blancoi* A. DC.) (FIG. 8).

Moreover, the velvet apple (*Diospyros blancoi* A. DC.) extract was tested for ability to inhibit the invasion of inflammatory cells in the mucous of the mice whose airways were sensitized with ovalbumin. Administration with the velvet apple (*Diospyros blancoi* A. DC.) significantly inhibited the accumulation of inflammatory cells including eosinophils, without damage to the epithelium (FIG. 9).

Goblet cells are known to be associated with asthma. The effect of the velvet apple (*Diospyros blancoi* A. DC.) on the growth of goblet cells in the airways was examined. The count of goblet cells in the epithelial lining of the airways was greatly reduced by the administration of the velvet apple (*Diospyros blancoi* A. DC.) extract (FIG. 10).

Therefore, the velvet apple (*Diospyros blancoi* A. DC.) extract of the present invention primarily inhibits the nuclear translocation of NF-κB, whose level is rapidly elevated in response to inflammatory stimuli, in turn suppressing the production of NO and $PGE_2$, the expression of iNOS and COX-2, and the release of IL-1β and TNF-α, and significantly down regulating Th2-mediated IL-4 and IL-13 production. In addition, the velvet apple extract was found to inhibit the increase of eosinophils in bronchoalveolar lavage fluid and to suppress the secretion of immunoglobulins and chemokines in bronchoalveolar lavage fluid and blood, as measured by in vivo tests on an ovalbumin-induced asthma mouse model. Also, the velvet apple extract is found to be almost free of cytotoxicity. Therefore, the extract is useful as an active ingredient of a pharmaceutical composition for preventing or treating various inflammatory disorders, allergic diseases, or asthma.

For application to medicines, the velvet apple (*Diospyros blancoi* A. DC.) extract of the present invention may be used in combination with one or more active ingredients identical or similar in function thereto. The composition of the present invention may further comprise a pharmaceutically acceptable additive. Examples of the additive available for the composition of the present invention include starch, gelatinized starch, microcrystalline cellulose, lactose, povidone, colloidal silicon dioxide, calcium hydrogen phosphate, lactose, mannitol, gum, Arabic rubber, pre-gelatinized starch, corn starch, powdered cellulose, hydroxypropylcellulose, opadry, sodium starch glycolate, carnauba wax, synthetic aluminum silicate, stearic acid, magnesium stearate, aluminum stearate, calcium stearate, white sugar, dextrose, sorbitol and talc. The pharmaceutically acceptable additive may be used in an amount of from 0.1 to 90 weight % based on the total weight of the composition of the present invention. The composition of the present invention may be in the form of a general drug agent which is administrable via oral or non-oral routes. That is, the composition of the present invention may be administered as various oral or non-oral dosage forms for clinical practice. In this regard, the velvet apple extract of the present invention may be usually formulated in combination with a diluent or excipient, such as a filler, a thickening agent, a binder, a wetting agent, a disintegrant, a surfactant, etc. Solid preparations intended for oral administration of the velvet apple extract of the present invention may take the form of tablets, pills, powders, granules, capsules, and the like. In regards to these solid agents, the velvet apple extract of the present invention is formulated in combination with at least one excipient such as starch, calcium carbonate, sucrose, lactose, or gelatin. In addition, a lubricant such as magnesium stearate, talc, or the like may also be added. Liquid preparations intended for oral administration include suspensions, internal use solutions, emulsion, syrups, and the like. In addition to a simple diluent such as water or liquid paraffin, various excipients, such as wetting agents, sweetening agents, aromatics, preservatives, and the like may be contained in the liquid preparations. Also, the composition of the present invention may be administered via a non-oral route. For this, sterile aqueous solutions, non-aqueous solvents, suspensions, emulsions, lyophilizates, suppositories, and the like may be used. Injectable propylene glycol, polyethylene glycol, vegetable oils such as olive oil, and esters such as ethyl oleate may be suitable for non-aqueous solvents and suspensions. The basic materials of suppositories include witepsol, macrogol, Tween 61, cacao butter, laurin butter, glycerol, and glycerogelatin.

According to purposes, the composition of the present invention may be administered orally or parenterally. For parenteral administration, the route through which the composition of the present invention is administered may be topical, intraperitoneal, intrarectal, subcutaneous, intravenous, intramuscular, or intracthoracic. The dose of administration may vary depending on patient's weight, age and gender, the state of health, diet, the time of administration, the route of administration, excretion rate and the severity of disease.

The effective dosage of the velvet apple (*Diospyros blancoi* A. DC.) extract in accordance with the present invention may vary depending on various factors, including the patient's weight, age, gender, state of health, diet, the time of administration, route of administration, excretion rate, severity of disease, etc. The velvet apple (*Diospyros blancoi* A. DC.) extract according to the present invention may be administered in a single dose or may be divided into two to six doses per day at a daily dose ranging from 0.0001 to 100 mg/kg, and preferably from 0.001 to 10 mg/kg.

To effect the prophylaxis and therapy of inflammatory diseases, allergic diseases, or asthma, the composition of the present invention may be used alone or in conjunction with surgical operation, radiotherapy, hormonal therapy, chemical therapy or an agent for biological modulation.

The composition of the present invention is also used to treat an inflammatory disease, an allergic disease, or asthma. Thus, a method for treating an inflammatory disease, an allergic disease, or asthma comprising administering a pharmaceutically effective amount of a velvet apple (*Diospyros blancoi* A. DC.) extract to a subject in need thereof forms another aspect of the present invention.

Also, contemplated in accordance with a further aspect of the present invention is a method for preventing an inflammatory disease, an allergic disease, or asthma, comprising administering a pharmaceutically effective amount of a velvet apple (*Diospyros blancoi* A. DC.) extract to a subject in need thereof.

The velvet apple (*Diospyros blancoi* A. DC.) extract according to the present invention may be administered at a dose of from 0.0001 to 100 mg/kg, and preferably at a dose of from 0.001 to 10 mg/kg. The effective dosage may varying depending on various factors, including the patient's weight, age, gender, state of health, diet, the time of administration, route of administration, excretion rate, severity of disease, etc.

The subject is a vertebrate, preferably a mammal, more preferably a rat, a rabbit, a guinea pig, a hamster, a dog or a cat, and most preferably an anthropoid such as chimpanzee or gorilla.

Administration may take an oral or a parenteral route. For parenteral administration, an intraperitoneal, intrarectal, subcutaneous, intravenous, intramuscular, intrauterine, intracerebroventricular or intrathoracic injection may be taken.

Examples of the inflammatory disease treatable in the present invention include dermatitis, atopy, conjunctivitis, perodontitis, rhinitis, otitis media, laryngopharyngitis, tonsillitis, pneumonia, gastric ulcer, gastritis, Crohn's disease, colitis, hemorrhoid, gout, ankylosing spondylitis, rheumatic fever, lupus, fibromyalgia, psoriatic arthritis, osteoarthritis, rheumatoid arthritis, periarthritis shoulder, tendonitis, tenosynovitis, peritendinitis, myositis, hepatitis, cystitis, naphritis, Sjogren's syndrome, multiple sclerosis, and acute and chronic inflammatory diseases, but are not limited thereto.

Having the inhibitory activity against the nuclear translocation of NF-κB, whose level is rapidly elevated in response to inflammatory stimuli, the velvet apple (*Diospyros blancoi* A. DC.) extract of the present invention can suppress the production of NO and $PGE_2$, the expression of iNOS and COX-2, and the release of IL-1β and TNF-α, and can significantly down regulate Th2-mediated IL-4 and IL-13 production. In addition, the velvet apple extract was found to inhibit the activation of eosinophils in bronchoalveolar lavage fluid, and to suppress the secretion of immunoglobulins and chemokines in bronchoalveolar lavage fluid and blood, as measured by in vivo tests on an ovalbumin-induced asthma mouse model. Also, the velvet apple extract is found to be almost free of cytotoxicity. Therefore, the extract can be used in the method for preventing or treating various inflammatory disorders, allergic diseases, or asthma.

In accordance with still a further aspect thereof, the present invention addresses a topical dermatologic agent for the prophylaxis and therapy of an inflammatory disease, an allergic disease, or asthma, comprising the velvet apple (*Diospyros blancoi* A. DC.) extract as an active ingredient. The inflammatory treatable with the topical dermatological agent may be selected from the group consisting of, but not limited to, edema, dermatitis, atopy, conjunctivitis, perodontitis, rhinitis, otitis media, laryngopharyngitis, tonsillitis, pneumonia, gastric ulcer, gastritis, Crohn's disease, colitis, hemorrhoid, gout, ankylosing spondylitis, rheumatic fever, lupus, fibromyalgia, psoriatic arthritis, osteoarthritis, rheumatoid arthritis, periarthritis shoulder, tendonitis, tenosynovitis, peritendinitis, myositis, hepatitis, cystitis, naphritis, Sjogren's syndrome, multiple sclerosis, and acute and chronic inflammatory diseases.

Primarily functioning to inhibit the nuclear translocation of NF-κB, whose level is rapidly elevated in response to inflammatory stimuli, the velvet apple (*Diospyros blancoi* A. DC.) extract of the present invention can suppress the production of NO and $PGE_2$, the expression of iNOS and COX-2, and the release of IL-1β and TNF-α, and can significantly downregulate Th2-mediated IL-4 and IL-13 production. In addition, in vivo tests on an ovalbumin-induced asthma mouse model demonstrate that the velvet apple extract inhibits the activation of eosinophils in bronchoalveolar lavage fluid and suppresses the secretion of immunoglobulins and chemokines in bronchoalveolar lavage fluid and blood. Also, the velvet apple extract is found to be almost free of cytotoxicity. Therefore, the extract is useful as an active ingredient of a topical dermatologic agent for preventing or treating various inflammatory disorders, allergic diseases, or asthma.

In addition to the velvet apple (*Diospyros blancoi* A. DC.) extract of the present invention as an active ingredient thereof, the topical dermatologic agent may comprise lipids, organic solvents, dissolving agents, thickening agents, gelling agents, softeners, anti-oxidants, suspending agents, stabilizers, foaming agents, aromatics, surfactants, water, ionic or non-ionic emulsifiers, fillers, sequestering agents, chelating agents, preservatives, vitamins, UV blocking agents, wetting agents, essential oils, dyes, pigments, hydrophilic or lipophilic activators, liposomes, and/or other general supplements used in the skin science field. These ingredients may be used in amounts that are generally accepted in the skin science field.

In the topical dermatologic agent, the velvet apple (*Diospyros blancoi* A. DC.) extract according to the present invention may be administered at a dose of from 0.0001 to 100 mg/kg, and preferably at a dose of from 0.001 to 10 mg/kg. The effective dosage may varying depending on various factors, including the patient's weight, age, gender, state of health, diet, the time of administration, excretion rate, severity of disease, etc.

Still another aspect of the present invention is a cosmetic composition for the prevention and amelioration of an inflammatory disease, an allergic disease, or asthma, comprising a velvet apple (*Diospyros blancoi* A. DC.) extract as an active ingredient.

The velvet apple (*Diospyros blancoi* A. DC.) extract of the present invention primarily inhibits the nuclear translocation of NF-κB, whose level is rapidly elevated in response to inflammatory stimuli, which, in turn, results in suppressing the production of NO and $PGE_2$, the expression of iNOS and COX-2, and the release of IL-1β and TNF-α, and significantly down-regulating Th2-mediated IL-4 and IL-13 production. In addition, it is demonstrated in an ovalbumin-induced asthma mouse model that the velvet apple extract inhibits the activation of eosinophils in bronchoalveolar lavage fluid, suppresses the secretion of immunoglobulins and chemokines in bronchoalveolar lavage fluid and blood, and is almost free of cytotoxicity. Therefore, the extract is useful as an active ingredient of a cosmetic composition for preventing and ameliorating various inflammatory disorders, allergic diseases, or asthma.

A cosmetic composition comprising the velvet apple extract of the present invention as an active ingredient may be formulated into general emulsion or water-soluble forms. Examples of the cosmetic forms to which the velvet apple extract of the present invention is applicable include solutions, gels, solid or paste preparations, oil-in-water emulsions, suspensions, microemulsions, microgranules or ionic liposomes, non-ionic vesicle dispersions, creams, skins, lotions, powders, ointments, sprays, conceal sticks, etc. Also, it may be prepared into a foam form or an aerosol form having a quantity of compressed propellant.

In addition to the velvet apple extract of the present invention, the cosmetic preparation may comprise lipids, organic solvents, dissolving agents, thickening agents, gelling agents, softeners, anti-oxidants, suspending agents, stabilizers, foaming agents, aromatics, surfactants, water, ionic or non-ionic emulsifiers, fillers, sequestering agents, chelating agents, preservatives, vitamins, UV blocking agents, wetting agents, essential oils, dyes, pigments, hydrophilic or lipophilic activators, liposomes, and/or other general supplements used in the skin science field.

In accordance with yet a further aspect thereof, the present invention addresses a health food for the prevention and amelioration of an inflammatory disease, an allergic disease, or asthma, comprising a velvet apple (*Diospyros blancoi* A. DC.) extract as an active ingredient.

Primarily functioning to inhibit the nuclear translocation of NF-κB, whose level is rapidly elevated in response to inflammatory stimuli, the velvet apple (*Diospyros blancoi* A. DC.) extract of the present invention can suppress the production of NO and $PGE_2$, the expression of iNOS and COX-2, and the release of IL-1β and TNF-α, and can significantly down-regulate Th2-mediated IL-4 and IL-13 production. In addition, the velvet apple extract was found to inhibit the activation of eosinophils in bronchoalveolar lavage fluid and to suppress the secretion of immunoglobulins and chemokines in bronchoalveolar lavage fluid and blood, as measured by in vivo tests on an ovalbumin-induced asthma mouse model. Also, the velvet apple extract is found to be almost free of cytotoxicity. Therefore, the extract is useful as an active ingredient of a health food for the prevention and amelioration of various inflammatory disorders, allergic diseases, or asthma.

Within the scope of the inflammatory disease fall edema, dermatitis, atopy, conjunctivitis, perodontitis, rhinitis, otitis media, laryngopharyngitis, tonsillitis, pneumonia, gastric ulcer, gastritis, Crohn's disease, colitis, hemorrhoid, gout, ankylosing spondylitis, rheumatic fever, lupus, fibromyalgia, psoriatic arthritis, osteoarthritis, rheumatoid arthritis, periarthritis shoulder, tendonitis, tenosynovitis, peritendinitis, myositis, hepatitis, cystitis, naphritis, Sjogren's syndrome, multiple sclerosis, and acute and chronic inflammatory diseases, but the disease is not limited thereto.

As a food additive, the velvet apple extract of the present invention may be properly used alone or in combination with other food ingredients according to a conventional method.

No particular limitations are imposed on the kind of foods to which the velvet apple extract can be added. Examples of such foods include meats, sausages, breads, chocolates, candies, confectionery, pizzas, ramen, other noodles, gums, dairy products such as ice-creams, various soups, beverages, teas, drinks, alcoholic beverages, vitamin complexes, and other healthy food supplements and are not limited thereto. All usually accepted health foods may contain the active ingredient according to the present invention.

A healthy beverage composition according to the present invention may further contain various fragrances or natural carbohydrates. Examples of such natural carbohydrates include monosaccharides, such as glucose and fructose, disaccharides such as maltose and sucrose, polysaccharides such as dextrin and cyclodextrin, and sugar alcohols such as xylitol, sorbitol, and erythritol. Also, sweeteners, e.g., natural sweeteners such as thaumatin and a stevia extract, or synthetic sweeteners such as saccharin and aspartame, may be added to the health food to which the active ingredient of the present invention is applied. The natural carbohydrate may be used in an amount of approximately 0.01~0.04 grams based on 100 mL of the beverage composition of the present invention, and preferably in an amount of approximately 0.02~0.03 grams.

In addition, the health food composition of the present invention may contain various nutrients, vitamins, minerals, electrolytes, flavors, colorants, pectic acid and salts thereof, alginic acid and salts thereof, organic acids, protective colloidal thickeners, pH modifiers, stabilizers, antiseptics, glycerin, alcohols, and carbonating agents used in carbonated beverages. Moreover, the composition of the present invention can contain fruit flesh for preparing natural fruit juices, fruit beverages, and vegetable beverages. These ingredients may be used individually or in combination. The ratio of these additives is not important, but is generally selected in a range of 0.01 to 0.1 weight parts per 100 weight parts of the composition of the present invention.

According to yet another aspect thereof, the present invention provides a method for treating an inflammatory disease, an allergic disease, or asthma, comprising administering a pharmaceutically effective amount of a velvet apple (*Diospyros blancoi* A. DC.) extract to a subject in need thereof.

Also contemplated according to yet still a further aspect of the present invention is a method for preventing an inflammatory disease, an allergic disease, or asthma, comprising administering a pharmaceutically effective amount of a velvet apple (*Diospyros blancoi* A. DC.) extract to a subject in need thereof.

Having inhibitory activity against the nuclear translocation of NF-κB, whose level is rapidly elevated in response to inflammatory stimuli, the velvet apple (*Diospyros blancoi* A. DC.) extract of the present invention is found to suppress the production of NO and $PGE_2$, the expression of iNOS and COX-2, and the release of IL-1β and TNF-α, and to significantly down-regulate Th2-mediated IL-4 and IL-13 production. In addition, in vivo tests on an ovalbumin-induced asthma mouse model show that the velvet apple extract can inhibit the activation of eosinophils in bronchoalveolar lavage fluid and can suppress the secretion of immunoglobulins and chemokines in bronchoalveolar lavage fluid and blood. Further, the velvet apple extract is found to be almost free of cytotoxicity. Therefore, the extract is useful in preventing or treating various inflammatory disorders, allergic diseases, or asthma.

The use of a velvet apple (*Diospyros blancoi* A. DC.) extract in a pharmaceutical composition for the prophylaxis and therapy of an inflammatory disease, an allergic disease, or asthma forms yet still another aspect of the present invention.

Also, the present invention provides the use of a velvet apple (*Diospyros blancoi* A. DC.) extract in a topical dermatologic agent for the prophylaxis and therapy of an inflammatory disease, an allergic disease, or asthma in accordance with an additional aspect thereof.

Another additional aspect of the present invention is the use of a velvet apple (*Diospyros Blancoi* A. DC.) extract in a cosmetic composition for the prevention and amelioration of an inflammatory disease, an allergic disease, or asthma.

Still another additional aspect of the present invention is the use of a velvet apple (*Diospyros blancoi* A. DC.) extract in a health food for the prevention and amelioration of an inflammatory disease, an allergic disease, or asthma The velvet apple (*Diospyros blancoi* A. DC.) extract of the present invention primarily inhibits the nuclear translocation of NF-κB, whose level is rapidly elevated in response to inflammatory stimuli, in turn suppressing the production of NO and $PGE_2$, the expression of iNOS and COX-2, and the release of IL-1β and TNF-α, and significantly down regulating Th2-mediated IL-4 and IL-13 production. In addition, in vivo tests on an ovalbumin-induced asthma mouse model demonstrate that the velvet apple extract can inhibit the activation of eosinophils in bronchoalveolar lavage fluid and can suppress the secretion of immunoglobulins and chemokines in bronchoalveolar lavage fluid. Also, the velvet apple extract is found to be almost free of cytotoxicity. Therefore, the extract can be effectively used in preparing an agent for preventing or treating various inflammatory disorders, allergic diseases, or asthma.

Advantageous Effects

As described above, the nuclear translocation of NF-κB, whose level is rapidly elevated in response to inflammatory stimuli, can be blocked by the velvet apple (*Diospyros blancoi* A. DC.) extract of the present invention, which can, in turn, suppress the production of NO and $PGE_2$, the expression of iNOS and COX-2, and the release of IL-1β and TNF-α, and can significantly down-regulate Th2-mediated IL-4 and IL-13 production. In addition, the velvet apple extract was found to inhibit the activation of eosinophils in bronchoalveolar lavage fluid and suppress the secretion of immunoglobulins and chemokines in bronchoalveolar lavage fluid and blood as measured by in vivo tests on an ovalbumin-induced asthma mouse model. Further, the velvet apple extract was found to be almost free of cytotoxicity. Therefore, the extract is useful as an active ingredient of a pharmaceutical composition for preventing or treating various inflammatory disorders, allergic diseases, or asthma.

Control: negative control treated with 0.1% DMSO;
LPS: positive control treated with 0.1% DMSO, followed by induction with 1 μg/ml LPS; and
Velvet apple: treated with 40 μg/mL velvet apple extract, followed by LPS induction.

Figure 2:
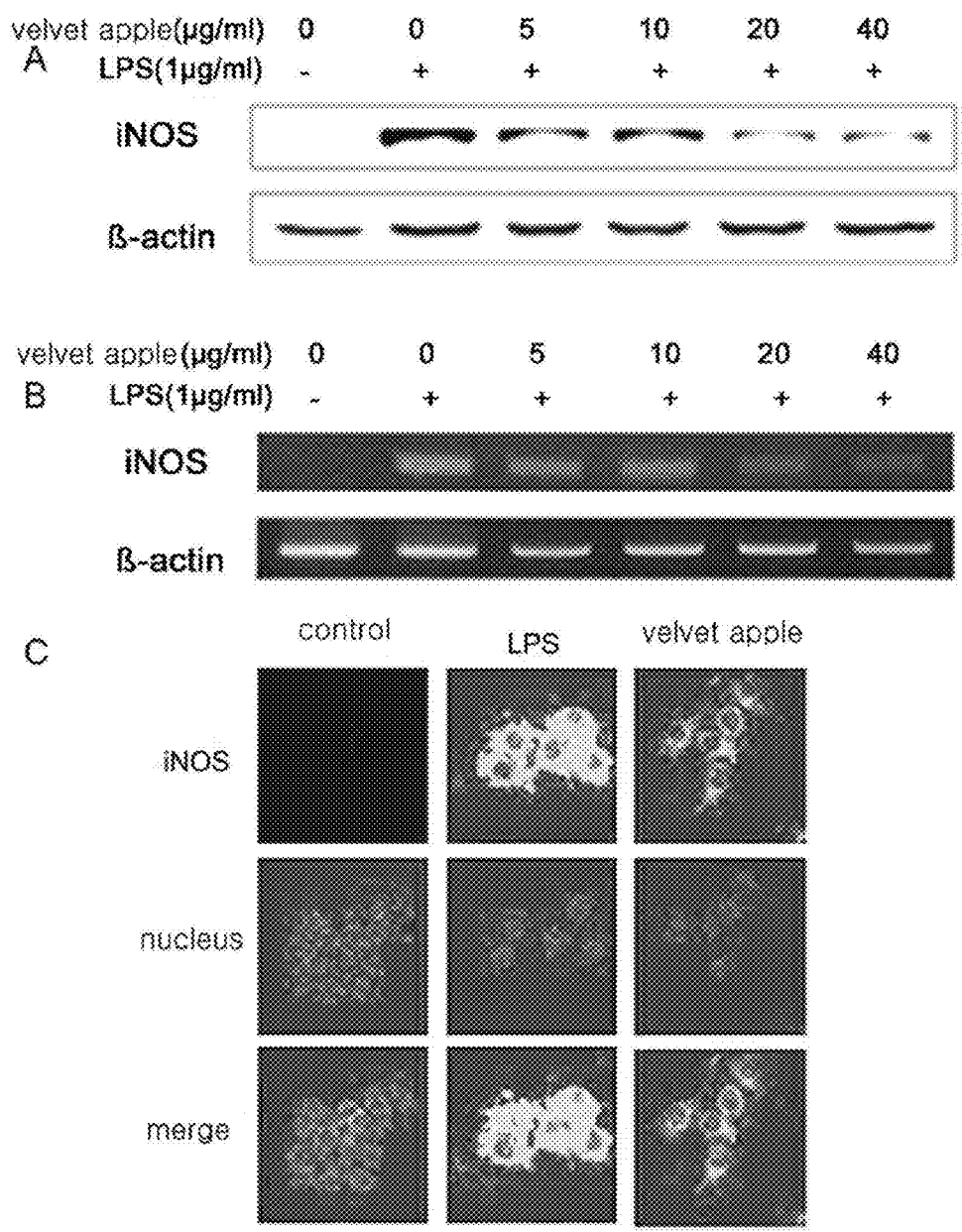

FIG. 2 shows the inhibitory activity of a velvet apple (*Diospyros blancoi* A. DC.) extract against iNOS expression:
a: Western blotting;
b: PCR; and
c: Immunofluorescence.

Figure 3:
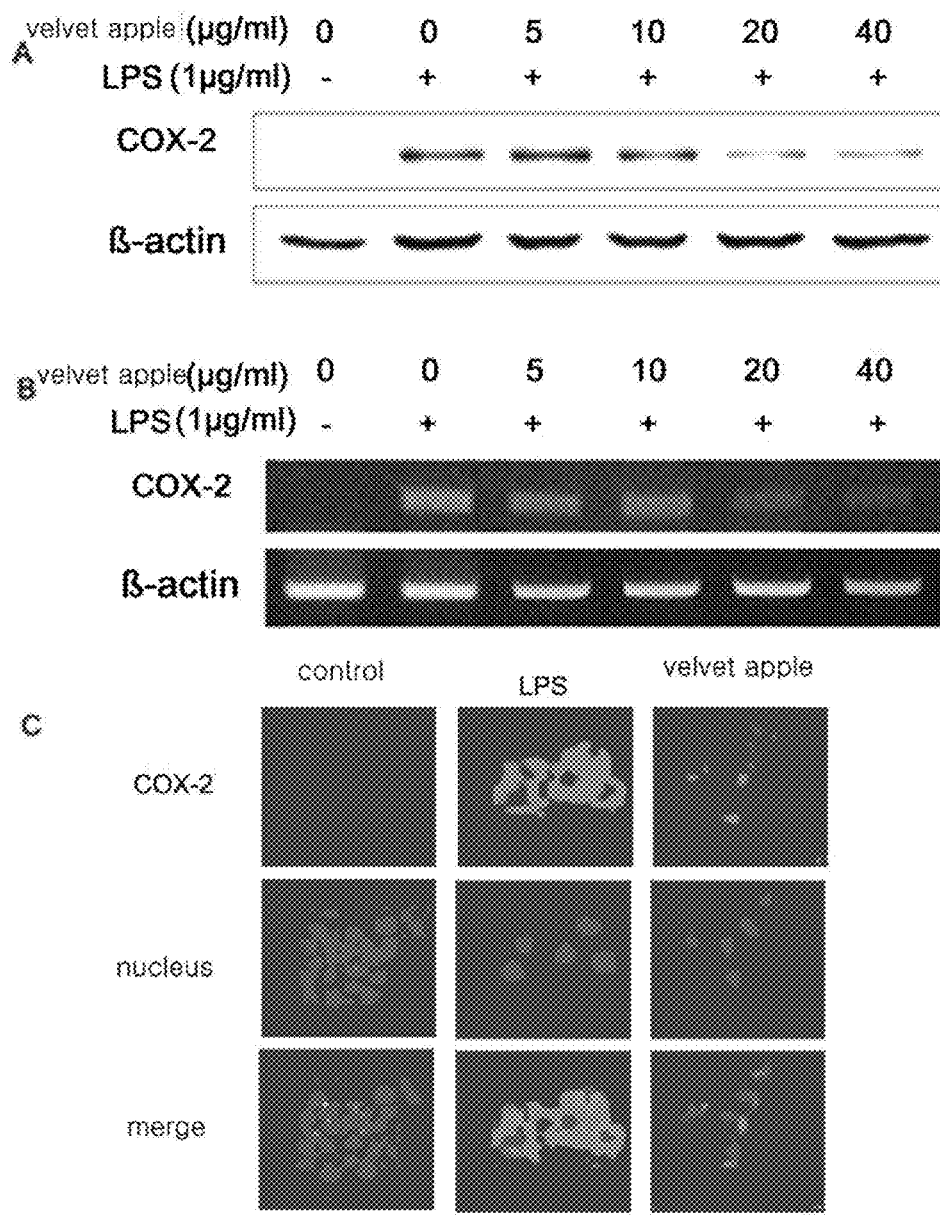

FIG. 3 shows the inhibitory activity of a velvet apple (*Diospyros blancoi* A. DC.) extract against COX-2 expression:
a: Western blotting;
b: PCR; and
c: Immunofluorescence.

Figure 4:
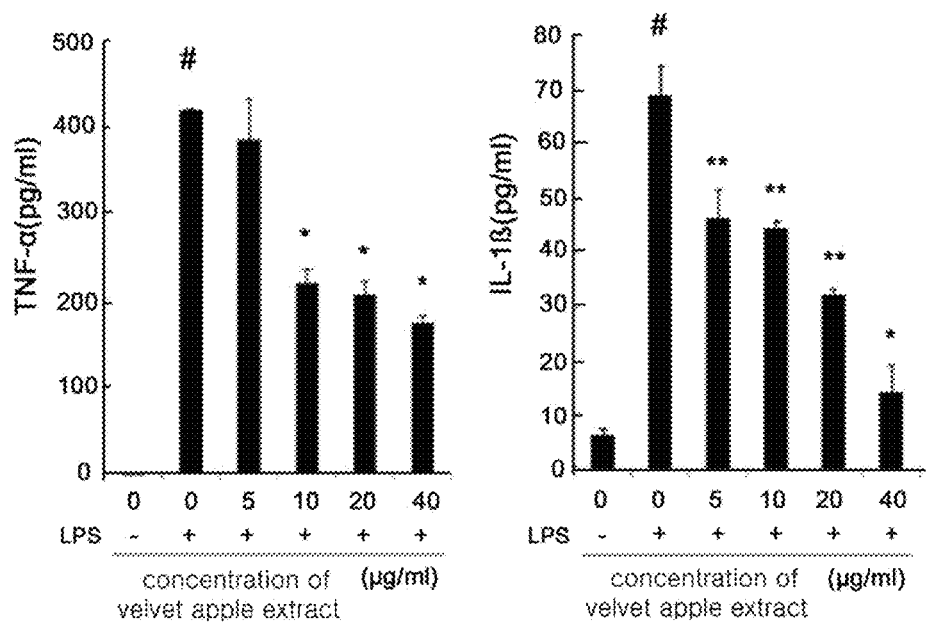

FIG. 4 shows the inhibitory activity of a velvet apple (*Diospyros blancoi* A. DC.) against the release of TNF-α and IL-1β (P value (*)≤0.005, (**)≤0.05).

Figure 5:
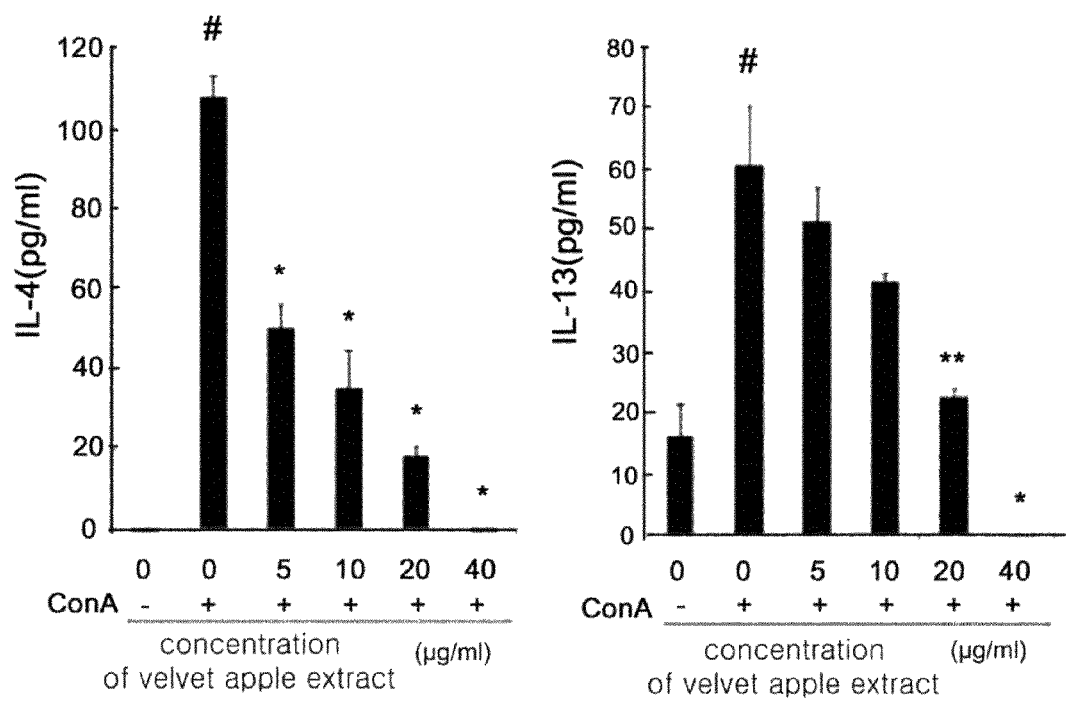

FIG. 5 shows the inhibitory activity of a velvet apple (*Diospyros blancoi* A. DC.) against the release of IL-4 and IL-13 (P value (*)≤0.005, (**)≤0.05).

Figure 6:
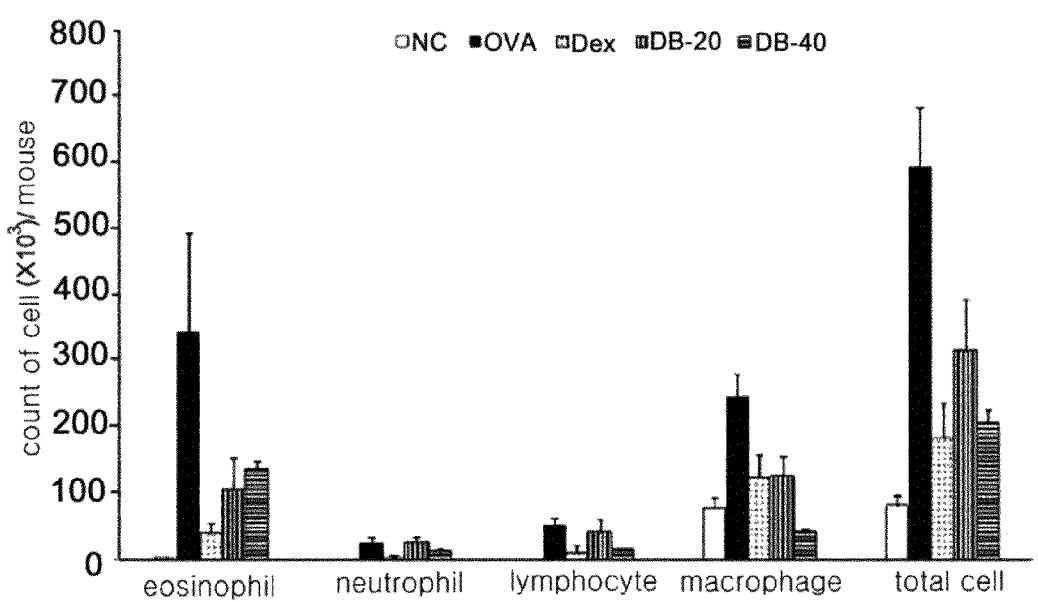

FIG. 6 is a graph showing effects of a velvet apple (*Diospyros blancoi* A. DC.) extract on the counts of total inflammatory cells and eosinophils in bronchoalveolar lavage fluid after airway sensitization:
NC; negative control without airways sensitization;
OVA; positive control with airways sensitization with ovalbumin;
Dex; treated with 30 mg/kg dexamethasone;
DB-20; treated with 20 mg/kg velvet apple extract; and
DB-40; treated with 40 mg/kg velvet apple extract.

Figure 7:
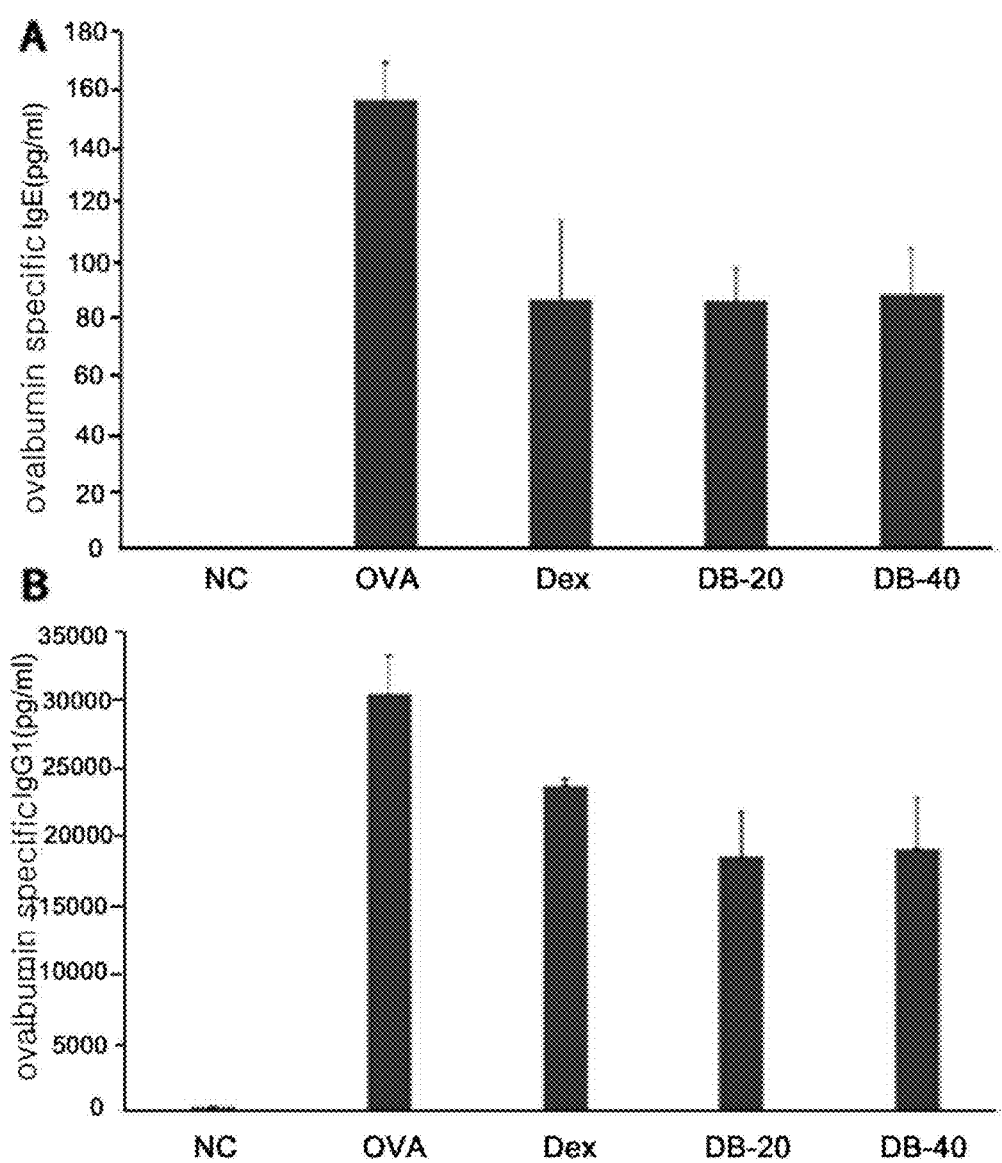

FIG. 7 shows serum immunoglobulin levels after airway sensitization:
NC; negative control without airways sensitization;
OVA; positive control with airways sensitization with ovalbumin;
Dex; treated with 30 mg/kg dexamethasone;
DB-20; treated with 20 mg/kg velvet apple extract; and
DB-40; treated with 40 mg/kg velvet apple extract.

Figure 8:
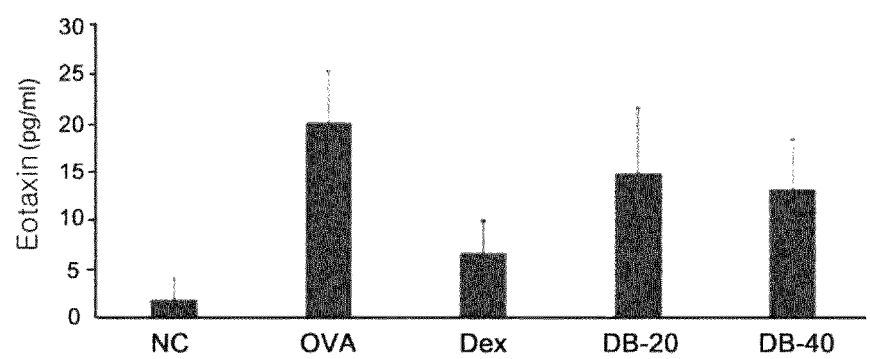

FIG. 8 is a graph showing levels of chemokines in bronchoalveolar lavage fluid after airway sensitization:
NC; negative control without airways sensitization;
OVA; positive control with airways sensitization with ovalbumin;
Dex; treated with 30 mg/kg dexamethasone;
DB-20; treated with 20 mg/kg velvet apple extract; and
DB-40; treated with 40 mg/kg velvet apple extract.

Figure 9:
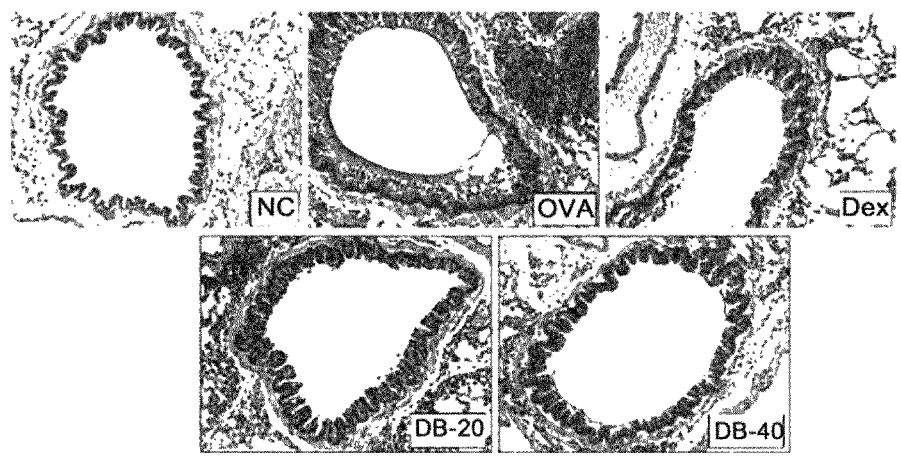

FIG. 9 shows images visualizing the effect of a velvet apple (*Diospyros blancoi* A. DC.) extract on the invasion of inflammatory cells into the epithelial lining of the airways of mice as stained with H&E;
NC; negative control without airway sensitization;
OVA; positive control with airway sensitization with ovalbumin;
Dex; treated with 30 mg/kg dexamethasone;
DB-20; treated with 20 mg/kg velvet apple extract; and
DB-40; treated with 40 mg/kg velvet apple extract.

Figure 10:
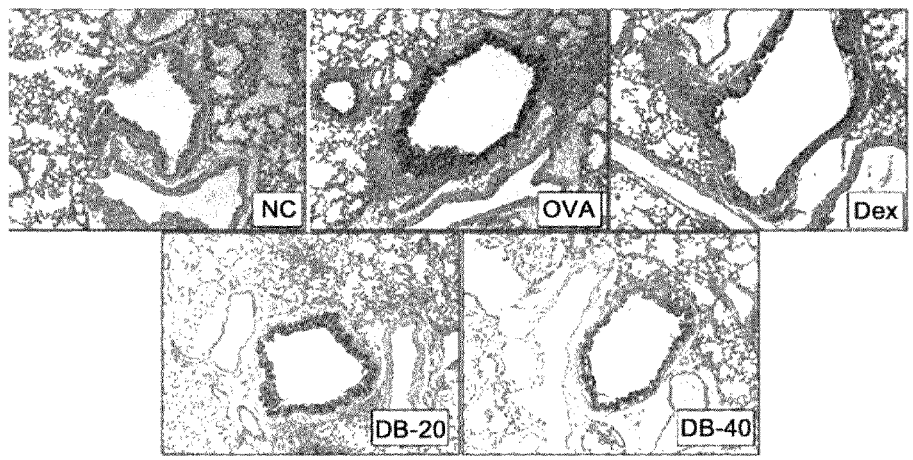

FIG. 10 shows images visualizing the effect of the effect of a velvet apple (*Diospyros blancoi* A. DC.) extract on the growth of goblet cells in the epithelial lining of the airway, as stained with PSA;
NC; negative control without airways sensitization;
OVA; positive control with airways sensitization with ovalbumin;
Dex; treated with 30 mg/kg dexamethasone;
DB-20; treated with 20 mg/kg velvet apple (*Diospyros blancoi* A. DC.) extract; and DB-40; treated with 40 mg/kg velvet apple (*Diospyros blancoi* A. DC.) extract.

MODE FOR INVENTION

A better understanding of the present invention may be obtained through the following examples which are set forth to illustrate, but are not to be construed as limiting the present invention.

EXAMPLE 1

Preparation of Velvet Apple (*Diospyros blancoi* A. DC.) Extract 1-1. Preparation of Methanol Extract of Velvet Apple (*Diospyros blancoi* A. DC)

Velvet apple (*Diospyros blancoi* A. DC.) originating from Costa Rica was obtained from the International Biological Material Research Center located in the Korea Research Institute of Bioscience & Biotechnology (hereafter KRIBB). To a powder obtained by drying and pulverizing 10 kg of velvet apple leaves, 20 liters of methanol was added. Extraction was continued for 24 hours at room temperature while stirring, followed by filtration to take the supernatant. This procedure was repeated three times, and a pool of the supernatant thus obtained was concentrated in a vacuum to afford 1.2 kg of a methanol extract of velvet apple (*Diospyros blancoi* A. DC.).

1-2. Preparation of Velvet Apple (*Diospyros blancoi* A. DC) Fraction

The methanol extract of velvet apple (*Diospyros blancoi* A. DC.) prepared in Example 1-1 was suspended in 1 L of water, mixed with one volume of 100% hexane and left while stirring. The procedure was conducted three times while removing the aqueous layers. As a result, a hexane extract measuring 4.02 g was obtained. After the removal of the hexane fraction, an equal volume of chloroform was added and stirred. Three repeats of this procedure afforded 1.43 g of a chloroform extract. The remaining suspension was extracted with ethyl acetate and butanol in the order in the same manner as above to give 1.76 g of an ethyl acetate extract and 1.98 g of a butanol extract. The remainder was concentrated to afford a 1.83 g of a water extract.

EXAMPLE 2

Assay of Velvet Apple (*Diospyros blancoi* A. DC) Extract and Fractions for Inhibitory Activity Against Cell Growth and NO Production 2-1. Assay for Cell Viability For use in examining the effect of the velvet apple (*Diospyros blancoi* A. DC.) extract on cell viability, Raw264.7 murine macrophage cells were suspended at a density of $1 \times 10^5$ cells/ml in DMEM (Dulbecco's Modified Eagle Medium, Gibco) supplemented with 5% FBS (Fetal Bovine Serum), and the suspension was aliquoted in an amount of 100 μL/well into 96-well plates. Four hours later, the adherent cells were incubated with each fraction for 24 hours and then with 10 μL of a 5 mg/ml MTT solution per well for an additional 4 hours. After the removal of the medium, 100 μL of DMSO was added to each well and absorbance was read at 570 mm Cell viability was expressed as percentages of absorbance at 570 nm for the negative control treated with 0.1% DMSO, as calculated according to the mathematic formula.

As can be seen in Table 1, the methanol extract and the water extract did not exhibit cytotoxicity in spite of a high dose thereof. On the other hand, the hexane, the chloroform, and the ethyl acetate extract exhibited cytotoxicity in a dose-dependent manner.

$$\text{Cell Viability (\%)} = \frac{\text{OD570 nm of Extract} - \text{Treated}}{\text{OD570 nm of Negative Control}} \times 100 \quad \text{Mathematic Formula 1}$$

TABLE 1

| Sample (μg/mL) | Cell Viability (%) |
|---|---|
| Negative Control | 100.00 ± 11.32 |
| MeOH Extract of Velvet Apple 5 | 101.53 ± 7.21 |
| MeOH Extract of Velvet Apple 10 | 99.26 ± 5.04 |
| MeOH Extract of Velvet Apple 20 | 102.88 ± 6.04 |
| MeOH Extract of Velvet Apple 40 | 94.81 ± 6.64 |
| MeOH Extract of Velvet Apple 50 | 94.53 ± 0.71 |
| Hexane Extract of Velvet Apple 5 | 58.82 ± 1.75 |
| Hexane Extract of Velvet Apple 10 | 47.90 ± 4.13 |
| Hexane Extract of Velvet Apple 20 | 42.58 ± 1.36 |
| Hexane Extract of Velvet Apple 40 | 33.15 ± 0.00 |
| $CHCl_3$ Extract of Velvet Apple 5 | 86.64 ± 6.27 |
| $CHCl_3$ Extract of Velvet Apple 10 | 69.21 ± 5.51 |
| $CHCl_3$ Extract of Velvet Apple 20 | 62.59 ± 0.91 |
| $CHCl_3$ Extract of Velvet Apple 40 | 49.70 ± 2.12 |
| EtAc Extract of Velvet Apple 5 | 85.95 ± 5.78 |
| EtAc Extract of Velvet Apple 10 | 82.57 ± 0.26 |
| EtAc Extract of Velvet Apple 20 | 74.29 ± 3.45 |
| EtAc Extract of Velvet Apple 40 | 69.10 ± 0.65 |
| EtAc Extract of Velvet Apple 50 | 59.64 ± 0.76 |
| BuOH Extract of Velvet Apple 5 | 95.03 ± 8.52 |
| BuOH Extract of Velvet Apple 10 | 87.19 ± 0.99 |
| BuOH Extract of Velvet Apple 20 | 86.75 ± 6.48 |
| BuOH Extract of Velvet Apple 40 | 80.15 ± 0.76 |
| Water Extract of Velvet Apple 5 | 102.59 ± 4.57 |
| Water Extract of Velvet Apple 10 | 99.06 ± 5.28 |
| Water Extract of Velvet Apple 20 | 102.85 ± 0.29 |
| Water Extract of Velvet Apple 40 | 97.12 ± 0.08 |

2-2 Assay for Inhibitory Activity Against NO Production

For use in examining the effect of the velvet apple (*Diospyros blancoi* A. DC.) extract on NO production, Raw264.7 cells were suspended in phenol-Red-free DMEM (Dulbecco's Modified Eagle Medium, Gibco) supplemented with 5% PBS (Fetal Bovine Serum), seeded at a density of $1 \times 10^5$ cells/well into 96-well plates and left for 4 hours to adhere to the bottom of each well. The adherent cells were incubated for 1 hour with 5, 10, 20, or 40 μg/mL samples, and then for 24 hours with 1 μg/mL LPS (lipopolysaccharide, Sigma). After being recovered from each well, 100 μL of the supernatant was transferred to new 96-well plates and reacted with an equal volume of Griess reagent (Sigma) at room temperature for 10 min. Absorbance was read at 540 nm on a microplate reader (Bio-Rad). A calculation curve was made using sodium nitrite and used to calculate levels of NO produced by the cells. The inhibitory activity against NO production of each sample is expressed as percentages of the level of NO produced in the LPS-treated group.

TABLE 2

| Sample (μg/mL) | NO Level (μM) | Inhibition (%) against NO Production |
|---|---|---|
| Negative Control | 1.51 ± 0.00 | |
| LPS | 23.11 ± 1.00 | |
| MeOH Extract of Velvet Apple 5 | 20.76 ± 0.19 | 10.15 ± 0.81 |
| MeOH Extract of Velvet Apple 10 | 22.31 ± 0.25 | 3.45 ± 1.08 |

TABLE 2-continued

| Sample (μg/mL) | NO Level (μM) | Inhibition (%) against NO Production |
|---|---|---|
| MeOH Extract of Velvet Apple 20 | 20.23 ± 0.06 | 12.45 ± 0.27 |
| MeOH Extract of Velvet Apple 40 | 17.75 ± 0.19 | 23.17 ± 0.81 |
| MeOH Extract of Velvet Apple 50 | 13.55 ± 0.88 | 41.36 ± 3.79 |
| Hexane Extract of Velvet Apple 5 | 22.71 ± 0.94 | 1.72 ± 4.06 |
| Hexane Extract of Velvet Apple 10 | 21.4 ± 1.13 | 7.66 ± 4.87 |
| Hexane Extract of Velvet Apple 20 | 22.00 ± 1.44 | 4.79 ± 6.23 |
| Hexane Extract of Velvet Apple 40 | 13.50 ± 3.07 | 41.55 ± 13.27 |
| CHCl3 Extract of Velvet Apple 5 | 23.73 ± 0.25 | 2.68 ± 1.08 |
| CHCl3 Extract of Velvet Apple 10 | 20.72 ± 0.00 | 10.34 ± 0.00 |
| CHCl3 Extract of Velvet Apple 20 | 16.82 ± 0.63 | 27.19 ± 2.71 |
| CHCl3 Extract of Velvet Apple 40 | 12.66 ± 0.38 | 45.19 ± 1.62 |
| EtAc Extract of Velvet Apple 5 | 20.10 ± 0.00 | 13.02 ± 0.00 |
| EtAc Extract of Velvet Apple 10 | 16.96 ± 0.44 | 26.62 ± 1.90 |
| EtAc Extract of Velvet Apple 20 | 17.58 ± 0.06 | 23.94 ± 0.27 |
| EtAc Extract of Velvet Apple 40 | 14.04 ± 0.69 | 39.26 ± 2.98 |
| EtAc Extract of Velvet Apple 50 | 10.67 ± 0.06 | 53.81 ± 0.27 |
| BtOH Extract of Velvet Apple 5 | 21.87 ± 0.25 | 5.36 ± 1.08 |
| BtOH Extract of Velvet Apple 10 | 21.65 ± 0.06 | 6.32 ± 0.27 |
| BtOH Extract of Velvet Apple 20 | 21.38 ± 0.56 | 7.47 ± 2.44 |
| BtOH Extract of Velvet Apple 40 | 17.09 ± 0.25 | 26.04 ± 1.08 |
| Water Extract of Velvet Apple 5 | 20.01 ± 0.75 | 13.40 ± 3.25 |
| Water Extract of Velvet Apple 10 | 20.81 ± 1.38 | 9.96 ± 5.96 |
| Water Extract of Velvet Apple 20 | 20.89 ± 1.63 | 9.57 ± 7.04 |
| Water Extract of Velvet Apple 40 | 21.16 ± 2.25 | 8.43 ± 9.75 |

As can be seen in Table 2, NO production was significantly lowered in the cells treated with the methanol, the chloroform, or the ethyl acetate extract, compared to LPS-treated cells, and in dose-dependent manners. Data from the assays for cell viability and NO production indicate that the methanol extract is excellent (Table 2).

EXPERIMENTAL EXAMPLE 1

Anti-Inflammatory Activity of Velvet Apple (*Diospyros blancoi* A. DC.) Extract in Raw264.7 Cell 1-1. Inhibitory Activity Against NF-Kappa B The translocation of NF-κB into the nucleus of RAW264.7 cells under an LPS-induced inflammation condition was examined using an immunofluorescence method. For this purpose, RAW264.7 cells were suspended at a density of $2 \times 10^4$ cells/mL in DMEM (Dulbecco's Modified Eagle Medium, Gibco) containing phenol-Red and 5% FBS (Fetal Bovine Serum), seeded into Permanox chambered plastic slides (Nunc, USA), and left for 4 hours to adhere to the slides. Thereafter, the cells were incubated for 1 hour with 40 μg/mL of each of the velvet apple (*Diospyros blancoi* A. DC.) extract and then for an additional 1 hour with 1 μg/mL lipopolysaccharide (LPS, Sigma). After the withdrawal of the medium, the cells were fixed at 4° C. for 30 min with ethanol, washed with phosphate buffered saline, and blocked with 3% bovine serum albumin at room temperature for 30 min. Then, the cells were reacted with the primary antibody [anti-NF-κB antibody (1:100)] at room temperature for 3 hours and washed sufficiently, followed by incubation with Texas red-conjugated secondary antibody (Santa Cruz Biotechnology, USA) at room temperature for 2 hours in a dark condition. Thereafter, the cells were washed three times with PBS, and mounted with a ProLong Gold Antifade reagent (Invitrogen, USA) before con-focal microphotography (LSM510m Carl Zeiss, Germany).

Figure 1:
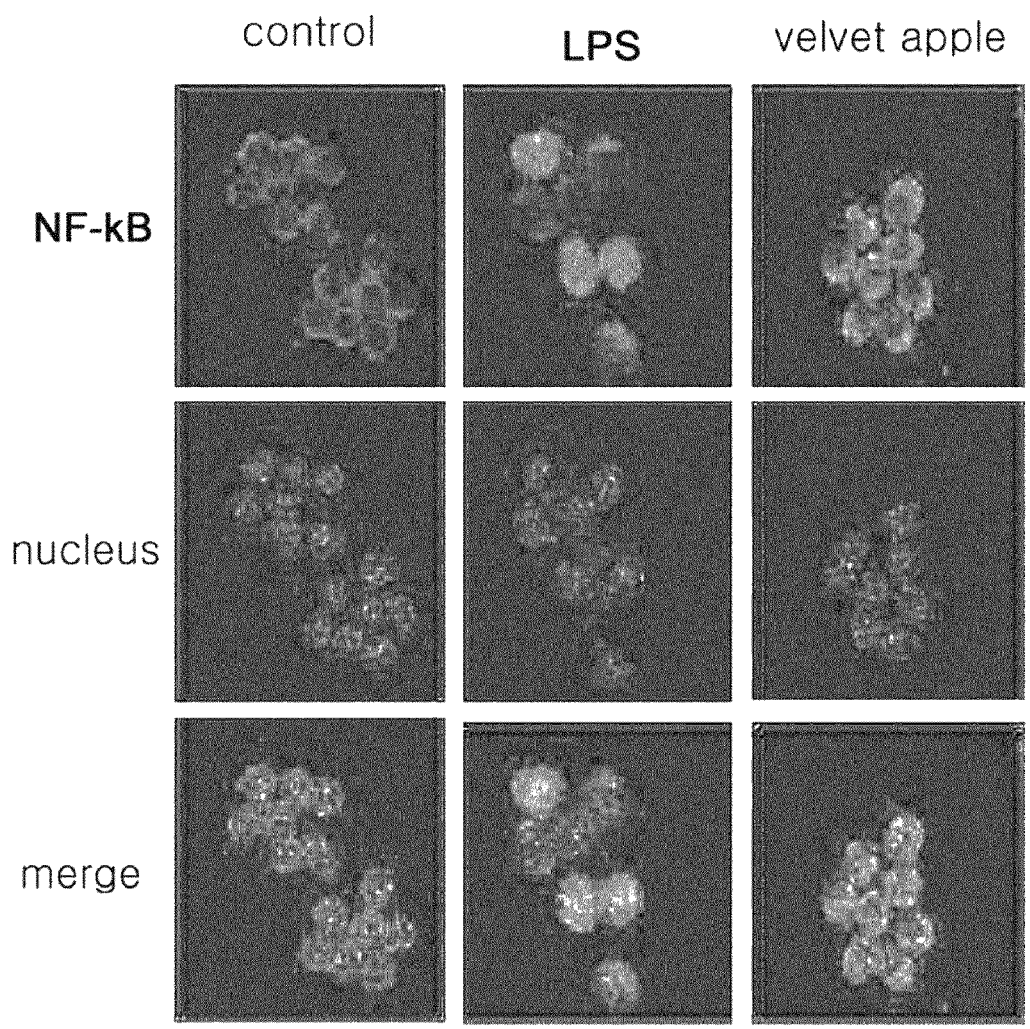
FIG. 1 shows images visualizing the inhibitory effect of a velvet apple (*Diospyros blancoi* A. DC.) extract on the translocation of NF-kappa B into the nucleus.

As shown in FIG. 1, a lower population of intranuclear NF-κB was observed in the cells co-treated with the velvet apple (*Diospyros blancoi* A. DC.) extract and LPS, compared to cells treated with LPS alone.

1-2 Inhibitory Activity Against Prostaglandin

In the Raw264.7 cells treated in the same manner as in Example 2-2, prostaglandin levels were measured using a $PGE_2$ assay kit (R&D systems, USA).

The results are summarized in Table 3. As is apparent from the data of Table 3, the velvet apple (*Diospyros blancoi* A. DC.) extract reduced the prostaglandin level elevated by LPS, in a dose-dependent manner.

TABLE 3

| Sample (μg/mL) | $PGE_2$ (pg/ml) | Inhibition (%) |
|---|---|---|
| Negative Control | 13.70 ± 0.26 | |
| LPS Treated | 522.80 ± 25.24 | |
| LPS + Extract of Ex. 1 (5) | 471.62 ± 9.11 | 9.78 ± 1.74 |
| LPS + Extract of Ex. 1 (10) | 465.38 ± 17.98 | 10.98 ± 3.44 |
| LPS + Extract of Ex. 1 (20) | 328.72 ± 22.21 | 37.12 ± 4.25 |
| LPS + Extract of Ex. 1 (40) | 240.87 ± 50.81 | 53.93 ± 9.72 |

EXPERIMENTAL EXAMPLE 2

Inhibitory Activity of Velvet Apple (*Diospyros blancoi* A. DC) Extract Against Expression of iNOS and COX-2 in Raw264.7 Cell The excellent inhibitory effects of the methanol extract of velvet apple (*Diospyros blancoi* A. DC.) on the production of nitric oxide and prostaglandin, obtained in Example 2 and Experimental Example 12, were confirmed at a protein and a ribonucleic acid level, as follows.

2-1 Western Blotting

Raw264.7 cells were seeded at a population of $1 \times 10^6$ cells into a 100 mm petri dish and induced into inflammation by treatment with LPS as in Example 1-1. After the withdrawal of the medium, the cells adherent to the bottom were homogenized with CelLytic™-Mammalian Tissue Lysis Reagent (Sigma, USA) containing a protease inhibitor cocktail (Roche, USA). After the centrifugation of the cell lysate for 20 min at 14,000 rpm, the supernatant was separated from the pellet and quantitatively analyzed for protein concentration with the aid of a protein assay kit (Bio-Rad, USA). Separately, the supernatant was mixed at a ratio of 4:1 with 5× loading buffer (0.156M Tris-HCl, pH 6.8, 2.5% SDS, 37.5% glycerol, 37.5 mM DTT) and boiled at 100° C. for 10 min. An amount of the sample corresponding to 40 μg of protein was loaded onto 4-12% SDS-PAGE gel and separated according to molecular weights for 2 hours in the presence of an electric field of 125 V. Then, the separated proteins were transferred for 1 hour onto PVDF membranes at 50 mA per gel. Protein-free portions of the PVDF membranes were blocked with skimmed milk, followed by sequential incubation with primary antibodies [anti-iNOS antibody (1:1000, Santa Cruz Biotechnology, USA), anti-Cox-2 antibody (1:1000, Santa Cruz Biotechnology, USA), anti-β-actin antibody (Santa Cruz Biotechnology, USA)] and a secondary antibody (anti-rabbit-IgG-HRP; Amersham Biosciences, UK). An ECL detection kit (Amersham Biosciences, UK) was used to develop protein blots on an X-ray film.

As can be seen in FIGS. 2A and 3A, the velvet apple (*Diospyros blancoi* A. DC.) extract decreased the expression of iNOS and COX-2 in the LPS-treated macrophage cells in a dose-dependent manner.

2-2 RNA Amplification (RT-PCR)

The cells treated as in Experimental Example 2-1 were washed with PBS and lysed with an RNA extraction reagent Trizol (Invitrogen, CA, USA). Five minutes later, the cell lysates were collected and completely mixed with 200 µl of chloroform for 15 sec, left for 3 min, and centrifuged for 15 min at 14,000 rpm. The supernatant was mixed with 500 µL of isopropyl alcohol for 10 min in a new tube. After centrifugation for 5 min at 10,000 rpm, the RNA pellet thus formed was dried at room temperature for 20 min. The dried RNA pellet was suspended in DEPC (Diethylpyrocarbonate, Sigma)-treated water. The RNA was quantitatively analyzed and used as a template to synthesize complementary DNA with the aid of RT-PreMix (AccuPower RT PreMix, Bioneer, Korea). iNOS was amplified from the cDNA in the presence of iNOS primers with the aid of PCR Premix (AccuPower PCR Pre-Mix, Bioneer, Korea).

As can be seen in FIGS. 2B and 3B, the expression level of both iNOS and COX-2 was rapidly elevated by LPS, but was reduced by the velvet apple (*Diospyros blancoi* A. DC.) extract in a dose-dependent manner even though the expression level was elevated by LPS.

2-3 Immunofluorescence

Inflammation induction, fixation and blocking of non-specific protein binding were performed for macrophages in the same manner as in Example 1-1. Incubation was carried out overnight at 4° C. with primary antibodies [anti-iNOS antibody (1:100) or anti-Cox-2 antibody (1:100)] and then at mom temperature for 2 hours with a secondary antibody (Santa Cruz Biotechnology, USA) conjugated with Texas red (Santa Cruz Biotechnology, USA) in a dark condition. Before reaction with the secondary antibody, the cells were washed three times with PBS. They were washed again with PBS and mounted with a ProLong Gold Antifade reagent before confocal microphotography.

As can be seen in FIGS. 2C and 3C, the cells expressed both iNOS and COX-2 at high levels upon treatment with LPS, whereas the levels of iNOS and COX-2 were significantly lowered in the cells co-treated with the velvet apple (*Diospyros blancoi* A. DC.) extract.

EXPERIMENTAL EXAMPLE 3

Inhibitory Activity of Velvet Apple (*Diospyros blancoi* A. DC) Extract Against Release of Cytokines in Raw264.7 Cells The velvet apple (*Diospyros blancoi* A. DC.) extract was analyzed for inhibitory activity against cytokine release in LPS-treated Raw264.7 cells. In this context, LPS-induced biosynthesis of IL-1β and tumor necrosis factor-α (TNF-α) was quantitatively determined using respective enzyme immunometric assay kits (mouse IL-1β Enzyme Immunometric Assay Kit and TNF-α Enzyme Immunometric Assay Kit; Assay designs, USA). After Raw264.7 cells were cultured in the same manner as in Example 2-2, the supernatant recovered from the cell culture was transferred in an amount of 50 µL/well to mouse immunoglobulin-coated 96-well plates and incubated for 2 hours while agitating. Then, the plates were washed four times with a wash buffer and incubated for 2 hours with 50 µL/well of the primary antibody anti-IL-1β or anti-TNF-α antibody. The cells were washed again and incubated for 30 min with a secondary antibody. After washing, a color was developed for 30 min with a substrate, and measured at 450 nm using a microplate reader.

As is understood from the data of FIG. 4, LPS induced the synthesis of both IL-1β and TNF-α, and the elevated levels of both IL-1β and TNF-α were reduced in a dose-dependent manner by the velvet apple (*Diospyros blancoi* A. DC.) extract.

EXPERIMENTAL EXAMPLE 4

Inhibitory Activity of Velvet Apple (*Diospyros blancoi* A. DC) Extract Against Release of Cytokines in Splenocyte Effects of the velvet apple (*Diospyros blancoi* A. DC.) on cytokine synthesis in splenocytes were examined. In this context, the spleen was aseptically excised from BALB/c mice (Orient, Korea) and homogenized in RPMI 1640 medium (GibcoBRL, USA) containing 10% PBS, 25 mM HEPES, 2 mM glutamine, penicillin (100 U/mL), and streptomycin (100 µg/mL) to form a single cell suspension. After the splenocyte suspension was centrifuged at room temperature at 1500 rpm for 10 min, the cell pellet thus obtained was dissolved at 37° C. for 10 min in 1 mL of red blood cell lysis buffer. This solution was mixed with 10 mL of PBS and centrifuged at room temperature at 1500 rpm for 5 min followed by discarding the supernatant. This procedure was repeated twice, after which the cell pellet was resuspended in RPMI 1640 supplemented with 10% FBS (GIBCO BRL, USA). In the cell suspension, cell counts were adjusted into $1 \times 10^6$ cells/mL, and 200 µL of the cell suspension was placed in each well of 96-well plates and incubated with various doses (0, 5, 10, 20, and 40 µg/mL) of the velvet apple (*Diospyros blancoi* A. DC.) extract at 37° C. for 1 hour in a 5% $CO_2$, humidified atmosphere, and then with 1 µg/mL concanavalin A (Sigma, USA) at 37° C. for 3 days in a 5% $CO_2$, humidified atmosphere so as to induce the expression of interleukin-4 (IL-4) and interleukin-13 (IL-13). Levels of IL-4 and IL-13 were determined using respective ELISA kits (R&D Systems, Minneapolis, USA) according to the manufacturer's introduction. A control was not treated with Con A.

As can be seen in FIG. 5, the ConA-induced expression of the cytokines was reduced by the velvet apple (*Diospyros blancoi* A. DC.) extract in a dose-dependent manner.

EXPERIMENTAL EXAMPLE 5

Effect of Velvet Apple (*Diospyros blancoi* A. DC) Extract on Inflammatory Cells and Eosinophils For use in examining effects of the velvet apple (*Diospyros blancoi* A. DC.) extract on inflammatory cells and eosinophils, SPF BALB/c mice 8 weeks old (weight: about 20 g) were purchased from Orient (Korea) and were intraperitoneally sensitized twice at regular intervals of two weeks with 200 µL of a suspension of 2 mg of aluminum hydroxide (Sigma A8222) and 20 µg of ovalbumin (Sigma A5503) in PBS (pH 7.4). Days 28, 29, and 30 after sensitization, a 1% ovalbumin solution in PBS was sprayed for 20 min into a closed container where the mice were confined, using an ultrasonic sprayer. A negative control group of 6 mice was not subjected to the airway sensitization, whereas a positive control group of 6 mice was subjected to airway sensitization with ovalbumin. For a comparison group, 6 mice were administered with dexamethasone at a dose of 30 mg/kg. The methanol extract of velvet apple (*Diospyros blancoi* A. DC.) suspended in PBS was orally administered at a dose of 20 mg/kg or 40 mg/kg into 6 mice of an experimental group one hour before the initial injection of the antigen. The mice were killed with excess pentobarbital (Sigma P3761) 48 hours after the final injection of the antigen, and were subjected to tracheotomy. Bronchoalveolar lavage fluid (BALF) was obtained by three rounds of suction of 0.6 mL per round through a cannula inserted into the trachea. Total inflammatory cells and eosinophils were counted as follows.

One hundred microliters of BALF from each group was placed on a slide. The cells were fixed to the slide by centrifugation in a cytospin (Hanil, Korea). After being stained with trypan blue, total living cells were counted in triplicate using a hemocytometer (Daigle I, et al., 2001). Eosinophils were visualized with a Diff-Quick reagent (Sysmex, Cat No. 38721, Swiss) and counted in the same manner.

The results are depicted in FIG. 6. As seen in the graph of FIG. 6, the ovalbumin-sensitized, PBS-administered, positive control was high in the count of total inflammatory cells, particularly in the count of eosinophils, compared to the non-sensitized, negative control (normal mice). The administration of the velvet apple (*Diospyros blancoi* A. DC.) extract reduced the increased count of eosinophils and the count of total inflammatory cells to a higher extent at a dose of 40 mg/kg than 20 mg/kg (FIG. 6).

EXPERIMENTAL EXAMPLE 6

Effect of Velvet Apple (*Diospyros blancoi* A. DC) Extract on Immunoglobulin Production 6-1. Inhibitory Effect of the Velvet Apple (*Diospyros blancoi* A. DC) Extract on IgE Production Serum IgE levels were measured to examine the inhibitory effect of the velvet apple (*Diospyros blancoi* A. DC.) extract on IgE production. For this purpose, sera from each group of Experimental Example 5 were 40-fold diluted and 100 μL of the dilution was reacted for 2 hours at mom temperature with 20 μg of the ovalbumin which had been used to induce the inflammation, in each well of 96-well plates.

Data from the antigen-antibody reaction, as shown in FIG. 7A, indicates that an elevated level of IgE was detected in mice sensitized with ovalbumin, but was significantly reduced upon treatment with the velvet apple (*Diospyros blancoi* A. DC.) extract.

6-2. Inhibitory Effect of Velvet Apple (*Diospyros blancoi* A. DC.) Extract on $IgG_1$ Production Serum $IgG_1$ levels were measured to examine the inhibitory effect of the velvet apple (*Diospyros blancoi* A. DC.) extract on $IgG_1$ production. For this purpose, sera from each group of Experimental Example 5 were 40-fold diluted and 100 μL of the dilution was reacted for 2 hours at mom temperature with 20 μg of the ovalbumin which had been used to induce the inflammation, in each well of 96-well plates.

Data from the antigen-antibody reaction, as shown in FIG. 7B, indicates that an elevated level of $IgG_1$ was detected in mice sensitized with ovalbumin, but was significantly reduced upon treatment with the velvet apple (*Diospyros blancoi* A. DC.) extract.

EXPERIMENTAL EXAMPLE 7

Effect of Velvet Apple (*Diospyros blancoi* A. DC) Extract on Chemokine Activity Eotaxin is known to selectively recruit and be active on cells which express CCR3, such as eosinophils, mast cells, and Th2 lymphocytes, which play an important role in allergic responses (Lilly, C. M. et al., Allergy Clin. Immunol, 2001). The level of the chemokine eotaxin in the bronchoalveoli of ovalbumin-sensitized mice was measured after the mice were administered with the velvet apple (*Diospyros blancoi* A. DC.) extract.

Eotaxin levels were determined using a sandwich-type enzyme-linked immunosorbent assay (ELISA). In detail, 100 μL of bronchoalveolar lavage fluid obtained from each group of Experimental Example 5 was reacted for 2 hours at room temperature with a cytokine antibody in each well of 96-well plates. Eotaxin levels were measured using an ELISA kit (BioSource International, Camarillo, Canada) responsive specifically to the cytokine according to the manufacturer's instruction.

As can be seen in FIG. 8, Ovalbumin-sensitized mice increased in eotaxin level which was reduced when they were administered the velvet apple (*Diospyros blancoi* A. DC.) extract.

EXAMPLE 8

Effect of Velvet Apple (*Diospyros blancoi* A. DC.) Extract on Invasion of Bronchial Inflammatory Cell For use in analyzing the effect of the velvet apple (*Diospyros blancoi* A. DC.) extract on the invasion of bronchial inflammatory cells, lung tissues from each group of Experimental Example 5 were fixed for 24 hours in 10% neutral buffered-formalin and embedded in paraffin. The embedded tissues were sectioned into slices 4 mm thick, stained with hematoxylin and Eosin Y (ThermoShandon, Pittsburgh, Pa.), and mounted with a Dako mounting medium (Dako cytomation, Denmark) for optical microscopy.

As seen in the optical images of FIG. 9, airway sensitization with ovalbumin induced asthma in the alveola and the bronchiole, resulting in an injury to epithelial cells and the invasion of inflammatory cells including eosinophils around the bronchiole while administration with the velvet apple (*Diospyros blancoi* A. DC.) extract, significantly reduced the population of inflammatory cells including eosinophils and almost healed the injured epithelia, which was coincident with the observation of Experimental Example 5 that counts of inflammatory cells and eosinophils were decreased when the velvet apple (*Diospyros blancoi* A. DC.) extract was administered.

EXPERIMENTAL EXAMPLE 9

Effect of Velvet Apple (*Diospyros blancoi* A. DC) Extract on Growth of Goblet Cells in the Epithelial Lining of the Airways To examine whether the velvet apple (*Diospyros blancoi* A. DC.) extract has an influence on the proportion of goblet cells in bronchial epithelial cells, lung tissues from each group of Experimental Example 5 were fixed for 24 hours in 10% neutral buffered-formalin and embedded in paraffin. The paraffin embedded tissues were sectioned into slices 4 mm thick, and goblet cells were visualized by periodic acid Schiff staining so as to evaluate the proliferation of goblet cells.

As shown in FIG. 10, the proportion of goblet cells in the epithelial cells of the bronchiole was very low in the negative control, but greatly increased in the asthma-induced groups, while the administration of the velvet apple (*Diospyros blancoi* A. DC.) significantly reduced the count of goblet cells, thus suppressing mucus secretion.

FORMULATION EXAMPLE 1

Preparation of Pharmaceutical Preparation 1-1. Preparation of Powder
Extract of Example 1-1: 2 g
Lactose: 1 g
The above ingredients were mixed and loaded into an airtight sac to produce a powder agent.

2. Preparation of Tablet
Extract of Example 1-1: 100 mg
Corn Starch: 100 mg
Lactose: 100 mg
Mg Stearate: 2 mg
These ingredients were mixed and prepared into tablets using a typical tabletting method.

1-3. Preparation of Capsule
Extract of Example 1-1: 100 mg
Corn Starch: 100 mg
Lactose: 100 mg
Mg Stearate: 2 mg
These ingredients were mixed and loaded into gelatin capsules according to a typical method to produce capsules.

1-4. Preparation of Pill
Extract of Example 1-1:1 g
Lactose: 1.5 g
Glycerin 1 g
Xylitol 0.5 g
These ingredients were mixed and prepared into pills each weighing 4 g.

5. Preparation of Granules
Extract of Example 1-1: 150 mg
Soybean Extract: 50 mg
Glucose: 200 mg
Starch: 600 mg
These ingredients were mixed in 100 mg of 30% ethanol and dried at 60° C. to give granules which were then loaded into sacs.

FORMULATION EXAMPLE 2

Preparation of Food 2-1. Preparation of Flour-Based Food
To 100 weight parts of flour were added 0.5~5.0 weight parts of the extract of Example 1-2 according to the present invention, and the flour mixture was used to make breads, cakes, cookies, crackers, and noodles.

2-2. Preparation of Soups and Gravies
The extract of Example 1-2 according to the present invention was added in an amount of 0.1~5.0 weight parts to 100 weight parts of typical soups or gravies to prepare health-improving soups or gravies for consumption with meat, processed products, or noodles.

2-3. Preparation of Ground Beef
The extract of Example 1-2 according to the present invention was added in an amount of 10 weight parts to 100 weight parts of typical ground beef to produce health-improving ground beef.

2-4. Preparation of Dairy Products
To 100 wt parts of milk was added 5~10 weight parts of the extract of Example 1-2 according to the present invention, and the milk was used to prepare various dairy products such as butter and ice-cream.

2-5. Preparation of Zen Food
Unmilled rice, barley, glutinous rice, and unshelled adlay were pre-gelatinized using a typical method, and dried and roasted before grinding into powder with a particle size of 60 mesh.

Black soybean, black sesame, and wild sesame were steamed according to a typical method, and dried and roasted before grinding into powder with a particle size of 60 mesh.

The extract of Example 1-3 according to the present invention was concentrated in a vacuum using a vacuum concentrator and dried in a convection oven, followed by grinding into powder with a particle size of 60 mesh.

The powders made of the grains, the seeds, and the extract of Example 1-3 according to the present invention were formulated at the following ratios to yield a zen food.

Grains (unmilled rice 30 wt parts, unshelled adlay 15 wt parts, barley 20 wt parts),
Seeds (wild sesame 7 wt parts, black soybean 8 wt parts, black sesame 7 wt parts),
Thy powder of the extract according to the present invention (3 wt parts),
*Ganoderma lucidum* (0.5 wt parts),
Foxglove (0.5 wt parts)

FORMULATION EXAMPLE 3

Preparation of Beverages 3-1. Preparation of Health Beverage
Five grams of the extract of Example 1-3 of the present invention was homogenously mixed with sub-ingredients such as liquid sucrose (0.5%), oligosaccharide (2%), sugar (2%), salt (0.5%), and water (75%), subjected to flash pasteurization, and packed in a container, such as a glass bottle, a PET bottle, and the like.

3-2. Preparation of Vegetable Juice
5 g of the extract of Example 1-3 according to the present invention was added to 1000 mL of typical tomato or carrot juice to give a health-improving vegetable juice.

3-3. Preparation of Fruit Juice
1 g of the extract of Example 1-3 according to the present invention was added to 1000 mL of typical apple or grape juice to give a health-improving fruit juice.

The invention claimed is:

1. A method of treating asthma in a human in need thereof comprising administering to said human a therapeutically effective amount of an extract of *Diospyros blancoi*, wherein the extract is at least one solvent selected from the group consisting of water, ethanol and methanol to treat the asthma in said human.

* * * * *